US012672786B2

(12) United States Patent
Stockmann et al.

(10) Patent No.: US 12,672,786 B2
(45) Date of Patent: Jul. 7, 2026

(54) METHOD FOR OPERATING A BLOOD PRESSURE MEASURING APPARATUS, AND APPARATUS FOR CARRYING OUT THE METHOD

(71) Applicant: REDWAVE MEDICAL GMBH, Jena (DE)

(72) Inventors: Chris Stockmann, Eisenberg (DE); Andreas Mainka, Jena (DE); Verena Dittrich, Erfurt (DE)

(73) Assignee: REDWAVE MEDICAL GMBH, Jena (DE)

( * ) Notice: Subject to any disclaimer, the term of this patent is extended or adjusted under 35 U.S.C. 154(b) by 659 days.

(21) Appl. No.: 18/011,990

(22) PCT Filed: Jun. 24, 2021

(86) PCT No.: PCT/EP2021/067270

§ 371 (c)(1),
(2) Date: Jan. 5, 2023

(87) PCT Pub. No.: WO2021/260082

PCT Pub. Date: Dec. 30, 2021

(65) Prior Publication Data

US 2023/0263411 A1 Aug. 24, 2023

(30) Foreign Application Priority Data

Jun. 25, 2020 (DE) .......................... 102020116750.4

(51) Int. Cl.
A61B 5/021 (2006.01)
A61B 5/00 (2006.01)
(Continued)

(52) U.S. Cl.
CPC ........ A61B 5/02108 (2013.01); A61B 5/0215 (2013.01); A61B 5/02225 (2013.01);
(Continued)

(58) Field of Classification Search
None
See application file for complete search history.

(56) References Cited

U.S. PATENT DOCUMENTS

| 6,647,287 B1 * | 11/2003 | Peel, III | ............ | A61B 5/02125 |
| | | | | 600/513 |
| 2003/0069490 A1 | 4/2003 | Narimatsu | ................... | 600/407 |

(Continued)

FOREIGN PATENT DOCUMENTS

| DE | 102017117337 A1 | 1/2019 | ............ A61B 5/022 |

OTHER PUBLICATIONS

Chen, C.-H., Nevo, E., Fetics, B., Pak, P. H., Yin, F. C. P., Maughan, W. L., & Kass, D. A. (1997). Estimation of central aortic pressure waveform by mathematical transformation of radial tonometry pressure. Circulation, 95(7), 1827-1836. https://doi.org/10.1161/01.cir.95.7.1827 (Year: 1997).*

(Continued)

*Primary Examiner* — Jacqueline Cheng
*Assistant Examiner* — Samuel C Kim
(74) *Attorney, Agent, or Firm* — Bodner & Bodner, PLLC; Christian P. Bodner; Gerald T. Bodner

(57) ABSTRACT

A method for operating a blood pressure measuring apparatus includes the steps of: applying a measuring apparatus, containing a pressure unit and/or a pressure measuring unit, to a measurement point on the body; initialising the measuring apparatus by carrying out a reference measurement and/or by carrying out defined position changes to the measurement point and determining person-specific initialisation parameters; storing the person-specific initialisation parameters in a memory and control unit; carrying out at least one blood pressure measurement by applying a counter pressure to the pressure unit in a sub-systolic low-pressure range; maintaining the applied counter pressure within a (Continued)

plateau phase having a predefined duration and recording blood pressure time curve data during the predefined duration; converting the recorded blood pressure time curve data over the initialisation parameters into arterial blood pressure data over time.

8 Claims, 28 Drawing Sheets

(51) Int. Cl.
  *A61B 5/0215*     (2006.01)
  *A61B 5/022*      (2006.01)
(52) U.S. Cl.
  CPC .... *A61B 5/7221* (2013.01); *A61B 2560/0223* (2013.01); *A61B 2562/0247* (2013.01)

(56)            References Cited

U.S. PATENT DOCUMENTS

| | | | | |
|---|---|---|---|---|
| 2003/0069507 | A1 | 4/2003 | Nishibayashi | 600/485 |
| 2011/0275944 | A1* | 11/2011 | Qasem | A61B 5/742 |
| | | | | 600/493 |
| 2016/0150983 | A1 | 6/2016 | Chowienczyk et al. | 600/485 |
| 2018/0263513 | A1* | 9/2018 | Qasem | A61B 5/7235 |
| 2020/0138305 | A1* | 5/2020 | Mukkamala | A61B 5/7278 |
| 2020/0229717 | A1 | 7/2020 | Dittrich et al. | |

OTHER PUBLICATIONS

The Notification Concerning Transmittal of International Preliminary Report on Patentability (Chapter I of the Patent Cooperation Treaty), in English, dated Jan. 5, 2023, which was issued by the International Bureau of WIPO in Applicant's corresponding international PCT application having Serial No. PCT/EP2021/067270, filed on Jun. 24, 2021.

The English translation of the International Preliminary Report on Patentability (Chapter I of the Patent Cooperation Treaty), dated Dec. 13, 2022, which was issued by the International Bureau of WIPO in Applicant's corresponding international PCT application having Serial No. PCT/EP2021/067270, filed on Jun. 24, 2021.

The Written Opinion of the International Searching Authority, in English, dated Sep. 28, 2021, which was issued by the International Bureau of WIPO in Applicant's corresponding international PCT application having Serial No. PCT/EP2021/067270, filed on Jun. 24, 2021.

The International Search Report, in English, dated Sep. 28, 2021, which was issued by the International Bureau of WIPO in Applicant's corresponding international PCT application having Serial No. PCT/EP2021/067270, filed on Jun. 24, 2021.

* cited by examiner

METHOD FOR OPERATING A BLOOD PRESSURE MEASURING APPARATUS, AND APPARATUS FOR CARRYING OUT THE METHOD

The invention relates to a method for operating a blood pressure measuring apparatus and to an apparatus for carrying out the method, and to a use of the method and of the apparatus.

Oscillometric blood pressure measuring apparatuses are known. These are usually operated by first placing a cuff around a limb, e.g. upper arm. The cuff is inflated by means of a pump. The pressure of the cuff interrupts the blood flow in a vessel running inside the limb. The pressure in the cuff is then released so that the blood flow in the depressurised vessel can be detected again. The blood pressure in this blood vessel is determined by the pressure currently prevailing in the cuff. With such a method, for example, the mean arterial pressure and from this the systolic as well as the diastolic blood pressure in the blood vessel can be determined. In particular, the lowering of blood pressure at night during sleep plays an important role in the detection and therapy of high blood pressure or stress.

The prior art shows that for the non-invasive determination of blood pressure, a cuff must be applied to a limb. By inflating this cuff by at least 20 mmHg above the expected systolic blood pressure, a pressure of at least 140 mmHg (often 180 mmHg) is exerted on the user's limb. This is not only uncomfortable, but can be painful under certain circumstances. In addition, sleep is considerably disturbed during night-time measurements, which influences the natural lowering of blood pressure and thus falsifies the result. Due to the required release rate of the pressure in the cuff of <7 mmHg/sec, such a blood pressure measurement takes between 30 sec to 90 sec.

Modifications of these systems can determine the blood pressure on the basis of the signals during the inflation phase. However, these require a similarly high target pressure in the system of, for example, 20 mmHg above the expected systole. Also, the inflation rate should not exceed 7 mmHg/sec. Thus, the main disadvantages of this technology remain.

Systolic and diastolic blood pressure are key parameters for characterising the circulatory status of a patient or user. However, in many cases these parameters are not sufficient. Very often, detailed statements about the haemodynamics of a living being can only be made if more detailed knowledge of the vascular properties is available. This cannot be obtained from a simple blood pressure measurement of the known kind, and, instead, an analysis of the pulse waves is necessary for this.

Systems known from the prior art that allow measurements without cuffs (for example via optical sensors or piezoelectric sensors, as in tonometry) exert less stress on the user, but they are not able to determine valid blood pressure values. They require calibration of the measurement values before each individual measurement. These are the basis for the transformation used to determine blood pressure. The preceding cuff measurement is thus still required and defines the accuracy of the system.

Other known devices for pulse wave analysis control in a targeted manner a constant pressure, a so-called pressure plateau, which is held for several seconds, usually 10 seconds. This method alone is also not able to determine the blood pressure and always requires a directly preceding standard measurement as a reference.

Another very big problem with systems that currently try to determine blood pressure without a cuff is that when performing a pulse wave analysis, a single formula is used for transformation (general transfer function) for the entire population, which is associated with a significant lack of precision and loss of quality. Furthermore, only one reference blood pressure is given for calibration.

The object is therefore to describe a method with which the blood pressure can be determined without the known process of inflating and deflating a blood pressure cuff. Specifically, a target pressure of 100 mmHg should not be exceeded, and the method sought should allow a valid blood pressure measurement and pulse wave analysis with additional haemodynamic parameters. This should make it possible to improve the quality of the measurement data during a spot measurement, a long-term measurement and a night-time measurement by increasing the wearing comfort, reducing the stress on the user, shortening the measurement duration of a single measurement, and increasing the number of measurements per measurement series.

The object is achieved with a method for operating a blood pressure measuring apparatus having the features of one or more of the claims and an apparatus for carrying out the method having the features of one or more of the claims as well as a use of the method and the apparatus.

The method for operating a blood pressure measuring apparatus comprises the following method steps:

A measuring apparatus containing a pressure unit and a pressure measuring unit is applied to a measurement point on the body.

Afterwards, the measuring apparatus is initialised by carrying out a reference measurement and/or by carrying out defined position changes of the measurement point and determining person-specific initialisation parameters.

Afterwards, the person-specific initialisation parameters are stored in a memory and control unit.

At least one blood pressure measurement is then performed by applying a counter pressure to the pressure unit in a sub-systolic low-pressure range.

The applied counter pressure is maintained within a plateau phase having a predetermined duration, and temporal blood pressure curve data are registered during the predetermined duration.

Afterwards, the registered temporal blood pressure curve data are converted into temporal arterial blood pressure data via the initialisation parameters.

The initialisation by execution of the reference measurement is carried out in one embodiment with the following steps:

A measurement pressure is applied to the measuring apparatus in a supra-systolic pressure range.

The measurement pressure is then released from the measuring apparatus and the temporal pressure curve is registered in the control and memory unit during the release process.

An oscillating pulse component is then extracted from the temporal pressure curve during the release process in conjunction with a storing of a series of data regarding individual pulse waves in the control and memory unit.

Afterwards, a signal analysis of the individual pulse waves and data comparison with a given pulse wave signal model is carried out by the control and memory unit.

On this basis, a person-specific transfer function is determined from the data comparison, and the determined transfer function is stored as a person-specific initialisation parameter in the control and memory unit.

In one embodiment, the previously mentioned signal analysis of the individual pulse waves is performed with the following steps:

The form of the particular pulse wave is evaluated and the pulse wave in question is classified in an evaluation unit and stored in an internal memory.

Thereafter, an assembly and transformation of pulse waves from at least one classification into at least one pulse wave signal model reproducing the features of the arterial pulse wave is performed.

The measured pulse wave curves are then adapted to the at least one pulse wave signal model, and at least one transfer function is determined for the particular pulse wave signal model.

If necessary, in an advantageous embodiment of the method, a validation of the transfer function is carried out, wherein blood pressure curve data determined and stored during the blood pressure measurement at a given counter pressure are compared with given reference parameters.

In particular, when measuring blood pressure in the sub-systolic low-pressure range, an advantageous method design in the control and memory unit converts the measured temporal blood pressure curve data into arterial blood pressure values via an inverted person-specific transfer function determined from the initialisation step.

When measuring blood pressure in the sub-systolic low-pressure range in the control and memory unit, an iterated model-based blood pressure determination is carried out in one design of the method, wherein a deviation-minimising adaptation of parameters of a pulse wave signal model to the oscillating signal component of the measured blood pressure is performed via a signal transformation.

In the validation of the initialisation parameters, in one embodiment the model-based blood pressure determination in the sub-systolic low-pressure range is compared with the pulse wave signal model and a signal curve from the reference measurement, and the initialisation result that can be determined here is compared with the provided initialisation parameters.

In one design, the reference measurement is carried out by a catheter-like blood pressure measuring apparatus located in the blood vessel, wherein the time curve of the blood pressure determined in this process is compared with a temporal pressure curve determined in parallel at the measuring apparatus, and the transfer function is determined in this process.

For the initialisation and/or blood pressure measurement, an inflatable pressure cuff or a combination of a pressure cuff and a garment exerting a constant sub-systolic pressure can be used as the pressure unit of the measuring apparatus.

An inflatable pressure cuff in combination with an optical sensor can be used as the pressure unit of the measuring apparatus, wherein the inflatable pressure cuff is used for carrying out the reference measurement and the optical sensor is used for the blood pressure measurement in the sub-systolic low-pressure range.

An apparatus for carrying out a method comprises the following components:

A control and memory unit is provided, having a display, an internal initialisation program and a control program, a memory, a processor and bus as well as a plateau generator, and an initialisation and measuring unit controlled by the control and memory unit and having a pressure sensor and a pressure actuator.

The control and memory unit advantageously contains a digital signal-processing processor.

In an advantageous design, the control and memory unit has a communication unit for data exchange via an external communication network.

In an advantageous embodiment, an external evaluation unit is provided, wherein this can be coupled to the control and memory unit via a device interface.

The external evaluation unit can expediently have a display, a configuration program and/or an evaluation program and/or a user interface.

The described method and the described apparatus according to any of the preceding embodiments is provided for determining blood pressure parameters, in particular systole, diastole and further haemodynamic parameters by means of a pulse wave analysis.

The method and the apparatus are described in greater detail below on the basis of exemplary embodiments and method sequences. The appended FIGS. 1 to 28 serve for clarification. The same reference signs are used for like or functionally like parts.

Figure 1:
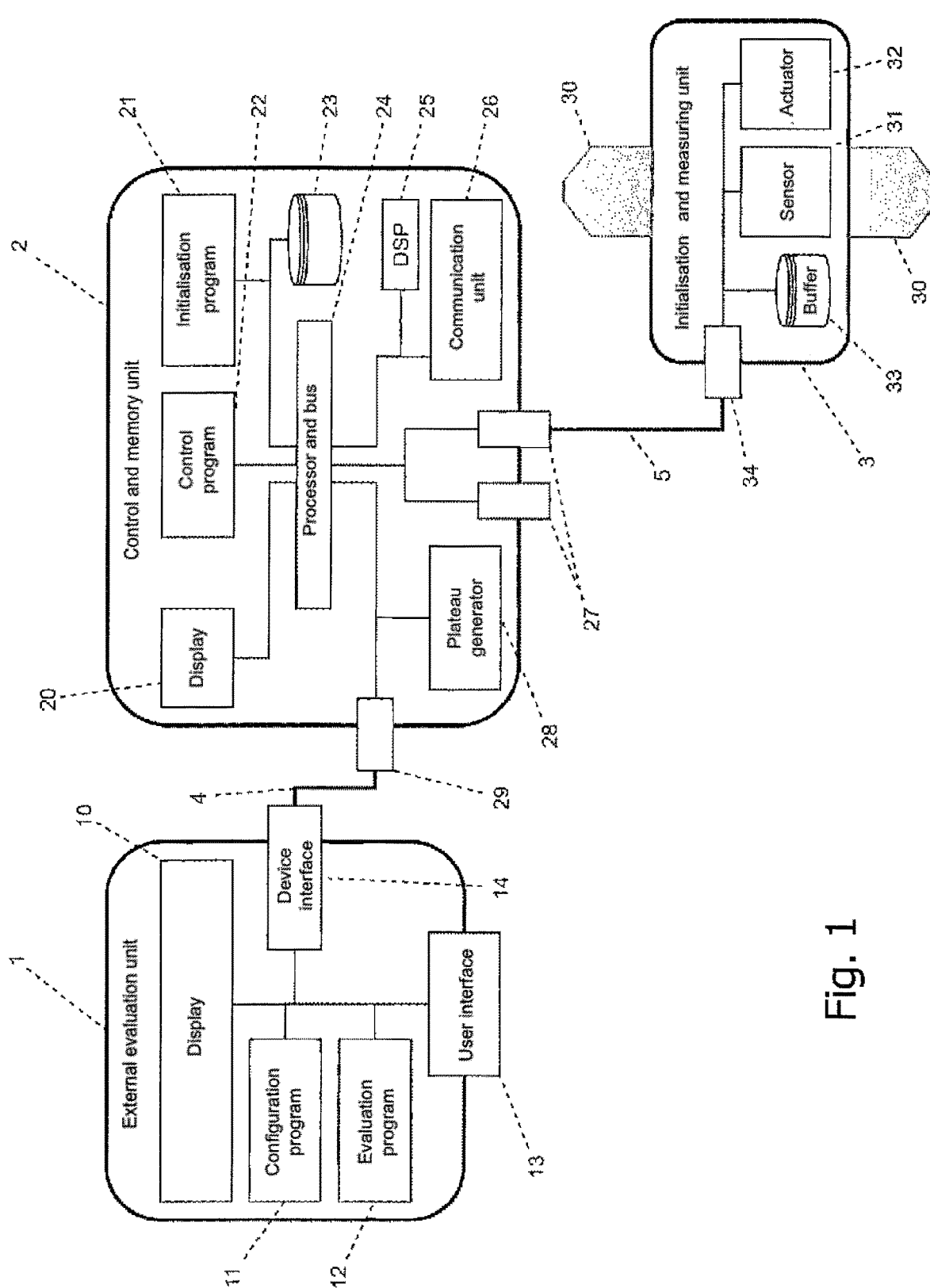
FIG. 1 shows an exemplary structure of a blood pressure measuring apparatus.

The system used to carry out the method according to the invention is designed to be as simple and robust as possible, so that this method with low counter pressure can be provided easily and inexpensively to surgery-based doctors in general, but also to patients at home.

The method for operating a blood pressure measuring apparatus comprises the following method steps in all the examples mentioned:

First, a measuring apparatus is applied with a defined pressure to a measurement point of body of the patient or user, the measuring apparatus comprising a sensor for attachment to a measurement point, a fastening unit and a pressure control unit for fastening the sensor with a defined pressure.

In a next step, the measuring apparatus is initialised by reference measurements and/or defined manoeuvres by the user, with person-specific parameters being determined here from the initialisation.

This is followed by the generation of individual algorithms based on the person-specific parameters, a registering and storing of the temporal signal curve at the sensor in a control and memory unit, and a signal analysis of the signal within the control and memory unit.

The method for operating a blood pressure measuring apparatus is carried out in particular with the following method steps:

A measuring apparatus with a defined pressure is applied to a measurement point, with the measuring apparatus comprising a sensor for attachment to a measurement point, a fastening unit and a pressure control unit for fastening the sensor with a defined pressure.

The measuring apparatus is then initialised by reference measurements and/or defined manoeuvres of the patient or user. These manoeuvres include, in particular, defined changes in the body position of the patient or user and/or the posture of individual body parts of the patient or user.

This involves a registering and storing of the temporal signal curve at the sensor in a control and memory unit.

Person-specific parameters are then determined from the initialisation with the following steps:

First, a pulse-like signal component is decomposed into data over individual periods to identify individual pulse waves.

Features, i.e. form features in the pulse waves, are then extracted. This is done by comparing the pulse waves from the reference measurement with the changed signals due to the aforementioned defined manoeuvres of the patient or user.

In conjunction with this, a classification of the individual pulse waves with the various identified features is carried out.

These features are transformed into suitable input parameters for the corresponding algorithms, and these are added to a database.

Individual algorithms are generated here on the basis of the patient-specific parameters, with the following steps being carried out:

A registering and storing of the temporal signal curve at the sensor in a control and memory unit and a signal analysis of the signal are carried out within the control and memory unit.

The following steps are carried out during the signal analysis:

The pulse-like signal component is decomposed into data over individual periods to identify individual pulse waves.

Subsequently, features are extracted from the pulse waves.

This is followed by an assessment of the extracted features by comparison with signals and features known from a database.

In a further step, the assessed features are evaluated to determine a blood pressure (such as brachial blood pressure, central blood pressure) and further haemodynamic parameters (such as pulse wave velocity, vascular aging, cardiac output, etc.).

The measuring apparatus can be applied for example by a cuff, a patch, a wristband, a clip and/or the like. For the selection of the sensor, in addition to a cuff, optical (PPG), electromagnetic (e.g. near-field radar) as well as mechano-electric sensors (such as piezoelectric sensors, strain sensors) and other (pressure-sensitive) sensors are possible in particular. The measurement point can be located practically anywhere on the body of the patient or user (e.g. on the wrist, forearm, upper arm, chest, neck, forehead, ear, etc.). The low counter pressure has a defined value and is constantly between 0 mmHg and 100 mmHg, for example.

Defined manoeuvres can be used to induce changes in the signal in a targeted manner in order to determine person-specific parameters on this basis.

These parameters are then suitable, for example, to determine coefficients, initial values, expected values and limits that are specific to the patient or user.

To generate individual algorithms based on the person-specific parameters, the following steps are carried out:

A database of suitable, parameterisable algorithms is created. This is then followed by a selection of class-specific algorithms on the basis of determined features. Lastly, the corresponding parameters are set as input for the respective algorithms.

Said method is used to detect and analyse pulse waves and to determine a blood pressure and other haemodynamic parameters.

In the following exemplary embodiments, the invention relates to a method for operating a blood pressure measuring apparatus and to the use of such a method for determining and analysing pulse waves.

The method is carried out by way of example with the following method steps and means:

Performing a BPM (blood pressure measurement) with low counter pressure on the measurement point. The sensor is placed on the skin and fixed with low, defined pressure (0<P<100 mmHg; for example 10 mmHg, 60 mmHg, 90 mmHg). The duration until the target pressure is reached for the measurement can then be reduced, for example to 0 sec for permanent counter pressure or to 5 sec for a short-term build-up of counter pressure. For example, a time interval of up to 30 sec is selected as the measurement duration at the target pressure.

For example, a so-called optical sensor represents a possible sensor that can be used. Here, it is possible to record a photoplethysmogram (PPG) with different wavelengths, e.g. green, red, infrared.

It is also possible to use a piezoelectric or electromagnetic sensor. Likewise, the configuration known from conventional oscillometry, consisting of an inflatable cuff and air, as well as a direct measurement using tonometry, can be used.

Strain sensors can also be used. A pressure that is changed by pulsation results in a strain, which leads to voltage changes and thus pulse waves. If necessary, ECG triggers can be used as optional support.

The measurement positions are basically free, for example, fingers, wrist, forearm, upper arm, upper body, chest, neck, forehead and/or ear can be used.

Parameters to be determined are blood pressure (systolic, MAP, diastolic, local (e.g. brachial) and central) as well as other haemodynamic parameters (pulse wave velocity, vascular aging, cardiac output/EF/SV).

The following exemplary steps can be implemented for this purpose:

To collect the raw data, the sensor is applied to the selected measurement point. Pulse waves are then recorded and stored over a period of several seconds.

A defined pressure on the sensor unit prevents a morphological change of the pulse waves caused by external influences.

Initialisation of the measuring apparatus is required and can be performed by special manoeuvres of the patient or user, such as changes in position and posture, for example transition from a lying to a sitting posture, movement of the arm downwards/centrally/upwards, changes in heart rate from rest (e.g. 75/min) to stress (e.g. >120/min), breathing commands (panting, deep and slow), speaking (reading text aloud) and walking.

If necessary, reference values from standard blood pressure measurements can also be used. In this way, the system learns the morphology changes caused by manoeuvres on a person-specific basis (since the external pressure remains constant). Such initialisations should be repeated regularly (e.g. 1×/year). This creates a frame of reference for a signal analysis that is adapted to the sensor, the measurement point and/or the pressure level.

Sensor fusion may be advantageous here. For example, a piezoelectric sensor can be combined with a PPG sensor and an ECG.

Dependencies may need to be taken into account here, such as heart rate, age, gender, smoking or non-smoking status, other medication and pre-existing conditions such as broken heart syndrome, atrial fibrillation (AFib) or heart failure.

The signal analysis is carried out by providing a list of algorithms which can be adapted to person-specific conditions by individual inputs. This takes into account the fact that not all algorithms are used with the same initialisation and weighting for every patient or user.

The calibration values thus provide for signal analysis: coefficients, initial values, expected values. Delimitations of correct/false are made possible as well as a detection of false positive/false negative.

An individual set of algorithms is therefore generated for each patient or user. The basis for this is the information from the initialisation.

For this purpose, selected, known or new models are used, for example pressure determination according to the Windkessel model and the determination of peripheral resistance R and compliance C in the pulse wave signal. The compliance C is the reciprocal elasticity.

When using the reservoir excess model, an estimate of the blood flow is made.

When using the Korteweg model, the dependence of the blood pressure on the pulse wave velocity is determined. The pulse wave velocity is determined by decomposing the pulse wave into forward-backward waves. So-called regression trees or a neural network can be used here.

FIG. 1 shows an exemplary structure of a blood pressure measuring apparatus. The blood pressure measuring apparatus contains an external evaluation unit 1 with a display 10 and a configuration program 11 as well as an evaluation program 12. Furthermore, a user interface 13 and a device interface 14 are provided. The user interface 13 is, for example, a keyboard or a corresponding control panel; the device interface allows data exchange with external devices.

The external evaluation unit can be, for example, a remote server, but also a locally available terminal device with a corresponding app. The device interface can be an interface for wireless or wired data transfer, for example a Bluetooth connection for communication with the terminal device, a USB connection or also a connection via a communication network. In any case, the external evaluation unit allows remote recording and remote evaluation of the registered blood pressure measurement data. The external evaluation unit 1 may, for example, be located in a consultant's office in the form of a computer that performs a remote query as to the status of a remote patient or user.

A control and memory unit 2 is provided for the actual execution of all blood pressure measurements. This unit contains a display 20 and a memory with an initialisation program 21 and a control program 22 running on it. A memory 23 and, if necessary, additionally a processor with bus 24 are provided for executing the programs. In addition, a digital signal-processing processor 25 may be provided which executes basic signal-processing routines; a communication unit 26 may also be provided, via which the, for example, voice inputs and outputs can take place. The control and evaluation unit further contains an interface 27 to the measuring unit and/or to an initialisation and measuring unit 3. Several measuring units can be connected, for example, to create a sensor fusion. Furthermore, an interface 29 to the external evaluation unit 1 is provided.

An initialisation and measuring unit 3 is provided for registering the blood pressure values at the body of the patient or user and/or for initialisation. The initialisation and measuring unit 3 can thus be used both for initialisation and for the actual measurement. However, designs are also possible in which the initialisation on the one hand and the measurement on the other are carried out by differently designed units.

The initialisation and measuring unit 3 shown here by way of example has a fastening apparatus 30 for fixing the measuring unit to the measurement point of the patient or user, for example a belt. A sensor 31 is used to detect the pressure, and an actuator 32 is used to apply pressure to the measurement point. The actuator can be formed in various ways, for example as an electromechanical actuator in the case of cuffless measurement, or a pump in the case of a measurement arrangement comprising a cuff.

A buffer 33 for temporary storing of the measurement data before data transfer and also an interface 34 to the control and evaluation unit are expediently provided.

The data are transferred and exchanged via a wired or wireless interface connection 4 and an interface connection 5, which can also be wired or wireless.

Possible exemplary embodiments of the measurement sensor 31 are in particular an acoustic sensor with corresponding internal components, an optical sensor, in particular a so-called PPG sensor, an electromagnetic sensor, a tonometric measurement sensor or also a patch or compression stocking with integrated strain sensors, which exerts a constant pressure on the corresponding measurement position.

For example, a blood pressure cuff or also a compression stocking can be considered as an actuator 32. The compression stocking offers the advantage of both strain measurement and compression. It can therefore serve as both sensor and actuator.

Possible exemplary measurement positions are, for example, the region of the upper arm, the forearm or the wrist, the thigh, the lower leg or the ankle. It is also possible to take a measurement in the ear canal or on the earlobe, on the forehead, on the neck or in the region of the thorax.

Figure 2:
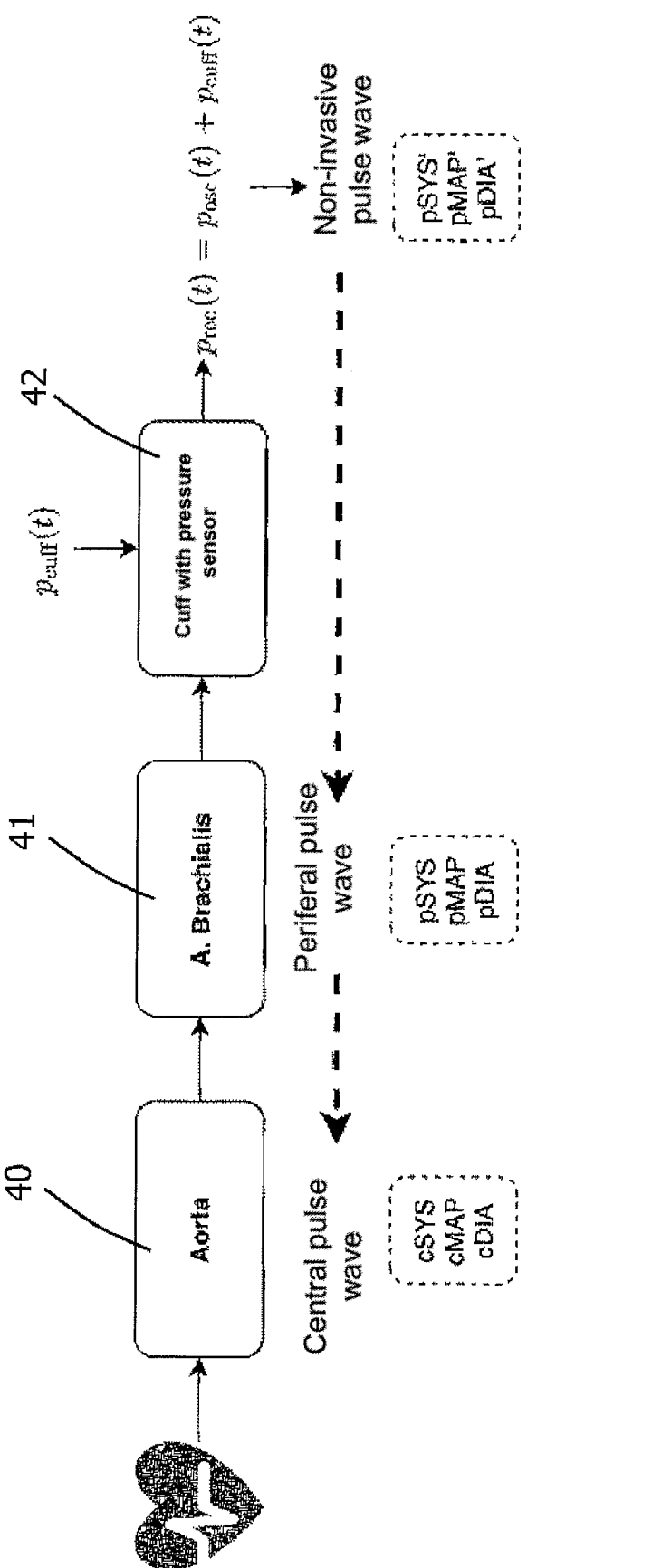
FIG. 2 shows a simplified illustration of the transfer path of the pulse wave generated by the heart from the source to the measurement sensor, in an exemplary manner for an oscillometric measurement.

FIG. 2 shows a simplified representation of the transfer path of the pulse wave generated by the heart from the source to the measurement sensor, as an example of an oscillometric measurement.

The method of drawing conclusions about the arterial pulse wave (both peripheral and central) and its properties from the non-invasively recorded oscillating measurement signal $p_{osc}(t)$ is, metrologically, a solution to a so-called inverse problem. The underlying source or its properties are to be determined from the observations, in this case the measurement signal.

FIG. 2 shows a simplified representation of the transfer portions of the measured pulse wave. This propagates from its source, i.e. the heart (or left ventricle), via the aorta 40 to the location of the peripheral measurement at the *A. brachialis* 41 (i.e. the brachial artery). When using an oscillometric measurement with a cuff 42, the oscillatory component $p_{osc}$ is detected in the inflation and/or deflation process of the recorded cuff pressure $p_{rec}$.

In order to be able to draw conclusions about the actual pressure conditions $p_{brach}$ in the artery from the measured pressure data $p_{rec}$ and in particular from the oscillatory component $p_{osc}$ measured in the process, the transfer properties under which the actual arterial pressure $p_{brach}$ translates into the measured pressure $p_{osc}$ under the influence of the cuff counter pressure $p_{cuff}$ must be known. Before the actual measurement process, it is therefore necessary to initialise the measurement arrangement in order to detect the transfer properties as accurately as possible, to model them, and to make them available for the subsequent regular measurements. The associated signal-processing operations will be explained in the following.

Figure 3:
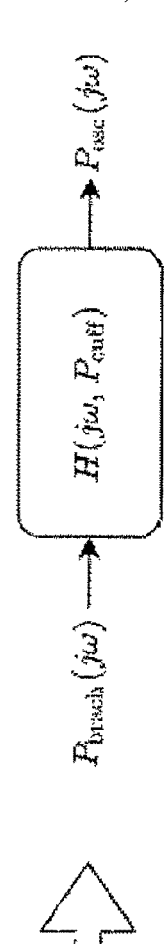
FIG. 3 shows an illustration of a dominant transfer element for low-pressure blood pressure determination (left) and a parameterised transfer function derived therefrom (right)
Figure 3:
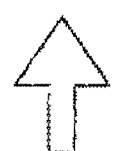
Figure 3:
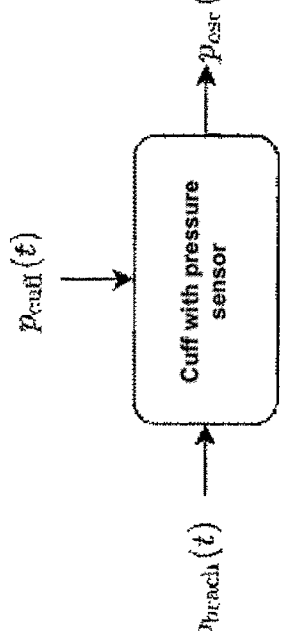
Figure 3:

FIG. 3 for this purpose shows an illustration of a dominant transfer element for low-pressure blood pressure determination on the left and a parameterised transfer function $H(j\omega, P_{cuff})$ derived therefrom on the right, which converts the arterial pressure $P_{brach}(j\omega)$ into the measured oscillatory pressure $p_{osc}(j\omega)$.

The consideration of these transfer properties for the oscillometric measurement can thus be approximately regarded as a transfer function with the cuff counter pressure $P_{cuff}$ as parameter, which sets the arterial pulse wave in the *A. brachialis* and the measured pulse signal (i.e. the oscillating component of $p_{rec}$) in relation to each other:

$$P_{osc}(j\omega)=P_{brach}(j\omega)H(j\omega,P_{cuff})$$

Under the simplified assumption of time invariance of the transfer properties for the duration of a pulse wave, the arterial pulse wave can now be determined from the measured pulse wave if the transfer function $H(j\omega, P_{cuff})$ and the associated constant cuff counter pressure $P_{cuff}$ are known.

$$P_{brach}(j\omega) = \frac{P_{osc}(j\omega)}{H_k(j\omega)}$$

Here, $H_k(j\omega)$ is the transfer function associated with the cuff counter pressure $P_{cuff}$. Thus, for a given counter pressure, the task is to determine the associated transfer function $$H_k(j\omega) = \frac{P_{osc}(j\omega)}{P_{brach}(j\omega)}.$$

When considering multiple blood pressure measurements taking place in a given period of time (e.g. during 24 h monitoring), it may be necessary to also take into account person-specific changes in the transfer properties occurring between the measurements. For this purpose, the transfer function $H_k(j\omega)$ can be divided in simplified fashion into two components. On the one hand, this is a person-specific transfer function invariant over the measurement period $H_{k,filt}(j\omega)$, which is dominated by the filter properties of the tissue surrounding the artery and the cuff. On the other hand, a person-specific time-variant transfer function, $H_{k,hemo}(j\omega)$, can be applied, which is dominated by the haemodynamic properties of the patient or user (e.g. arterial stiffness, arterial contraction, etc.) changing between the measurement times. $H_{k,hemo}(j\omega)$ may also contain diagnostically relevant information reflected in a particular change in pulse wave morphology and pulse wave characteristics. For example, $H_{k,hemo}(j\omega)$ can characterise the occurring person-specific differences between two blood pressure measurements recorded at the start and end of a day, respectively.

The pressure-dependent transfer function $H(j\omega, P_{cuff})$ or a derived set of transfer functions $H_k(j\omega)$ assigned to constant counter pressures $P_{cuff}$ is determined by a person-specific initialisation of the method.

After initialisation, a blood pressure measurement with a constant, sub-systolic counter pressure $P_{cuff}$ between 0 and 100 mmHg can be carried out in order to determine $P_{brach}(j\omega)$, and thus the sought blood pressure values, from the measured oscillating signal component $P_{osc}(j\omega)$ and the transfer function $H_k(j\omega)$ known from the initialisation. As a result of the low counter pressure, the patient load is considerably reduced and a possible influence on the blood pressure values, for example during a night-time measurement, is avoided.

In the following, the method will be presented on the basis of individual use cases.

Use Case A1

Figure 4:
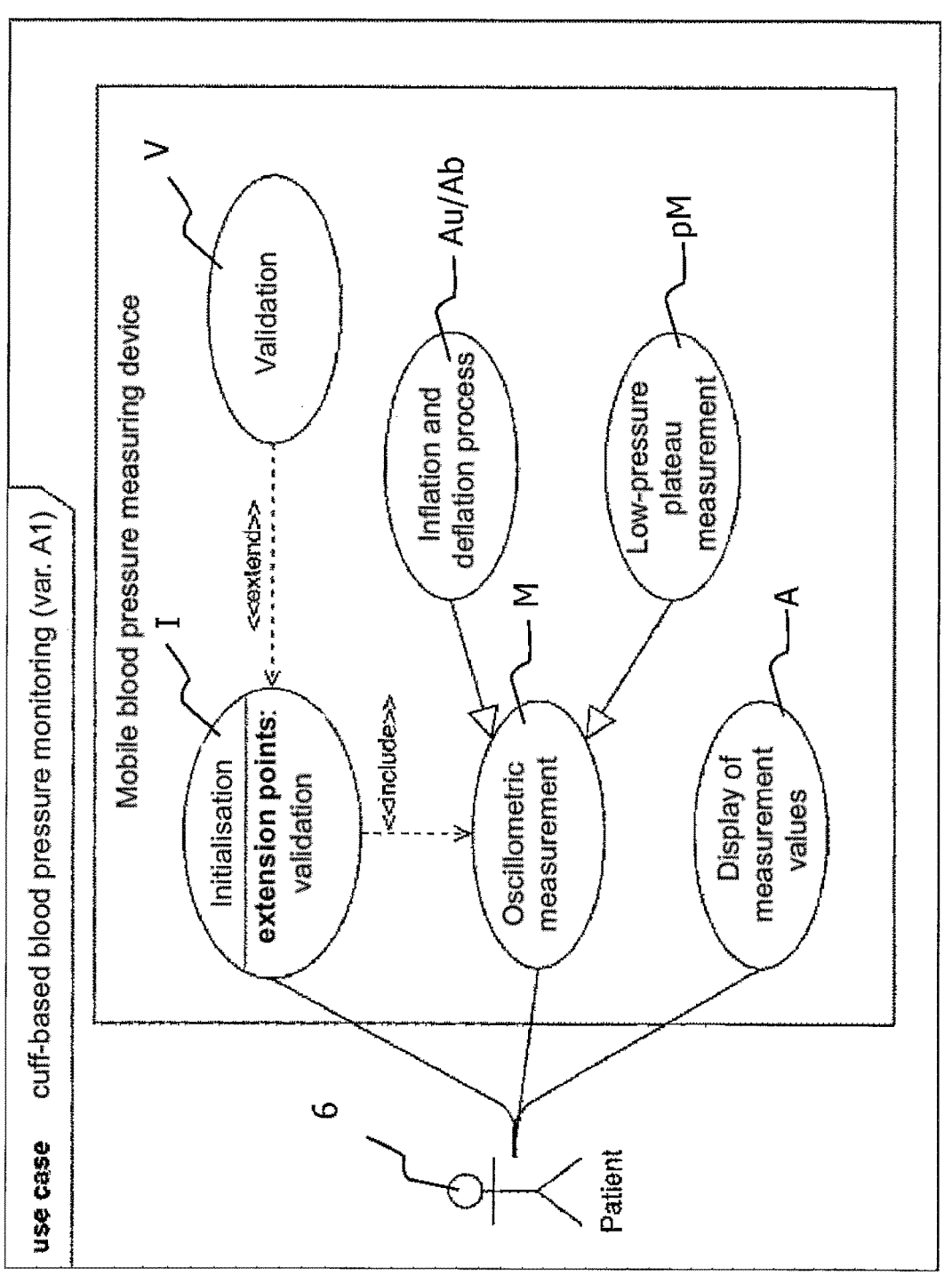
FIG. 4 shows an illustration of the exemplary use case A1.

Use case A1 is shown as an overview in FIG. 4. The exemplary embodiment of the method according to use case A1 can be used in conjunction with an oscillometric, cuff-based blood pressure measuring device for monitoring the patient's blood pressure in homecare use. In this case, the cuff is worn continuously by the patient/user 6 over the entire measurement period, in particular during a 24-hour measurement.

In use case A1, an initialisation I, an oscillometric measurement M and an evaluation of the measurement signals and vital parameters are autonomously performed by the blood pressure measuring device and initiated by the patient or user. If necessary, a validation V can also be carried out, in which the results of the initialisation are checked. Of course, there is a display A of the measurement values.

After initialisation I of the method, low-pressure plateau measurements pM are carried out at fixedly defined intervals during the measurement period for blood pressure monitoring, and during this process the cuff is inflated to a constant cuff pressure that is significantly below the expected systolic blood pressure.

At the start of the measurement period, i.e. at the start of the monitoring, the person-specific transfer functions dependent on the cuff pressure are determined via the initialisation I of the method. In a first embodiment of the method, a complete oscillometric measurement M is performed for initialisation, in which the cuff pressure is pumped to a peak value which is at least 20 mmHg above the expected systolic blood pressure.

From the complete oscillometric measurement M, the oscillating signal component, $p_{osc}$, of the cuff pressure during the inflation and/or deflation processes Au/Ab is extracted. The amplitude curve of $p_{osc}$ is used to determine the mean arterial blood pressure ($P_{MAP}$) as well as the diastolic ($P_{DIA}$) and systolic ($P_{SYS}$) blood pressure.

The person- and device-specific transfer functions for characterising the filter properties of the transfer element between the peripheral artery, e.g. the *A. brachialis*, and the measurement sensor are determined in the initialisation I of the method with the aid of the oscillating pressure signal $p_{osc}$, the non-oscillating cuff pressure $p_{cuff}$ (corresponds to the counter pressure generated by the cuff) and the blood pressure parameters $P_{DIA}$, $P_{MAP}$ and $P_{SYS}$.

For this purpose, individual pulse waves and person-specific parameters are extracted from the oscillating pressure signal $p_{osc}$ by means of a pulse wave analysis. On the basis of the parameters describing the pulse wave morphology and dynamics, the extracted pulse waves are classified and a pulse wave template is determined from a sub-set of suitable pulse waves and characterises the morphology of the arterial pulse wave.

A pulse wave signal model adapted to the time curve of the measured oscillating pressure signal $p_{osc}$ is now formed from the pulse wave template. In particular, the signal properties that can be influenced by the haemodynamics, e.g. the pulse wave interval, as well as features of the heart rhythm, for example extrasystoles or compensatory pauses, are taken into account. Taking into account the already determined blood pressure parameters, the pulse wave signal model can be transformed into a pulse wave signal (e.g. by scaling), which approximates the arterial pulse wave as accurately as possible.

With the pulse wave signal PWSig determined from the pulse wave model and the oscillating and non-oscillating cuff pressure time curves ($p_{osc}$ and $p_{cuff}$) known from the measurement, it is possible to determine the coefficients of the person-specific transfer functions $H_k$. This coefficient determination represents an optimisation problem in which the response of the transfer element modelled by $H_k$ should have, wherever possible, only a minimal error from the reference signal. In the initialisation, the pulse wave signal and the non-oscillating cuff pressure $p_{cuff}$ are the input signals, and the oscillating cuff pressure $p_{osc}$ is the reference signal.

In addition, the initialisation can take into account other parameters, such as information about the sensor, the patient or user, and the status of the measurement method. Examples here include cuff size as a possible sensor parameter, gender, age, height and weight as possible user or patient parameters, and previous initialisation results as possible status parameters.

The coefficients determined in the initialisation for describing the person- and device-specific transfer behaviour are stored in a memory unit of the blood pressure measuring device.

With the coefficients known from the initialisation, the transfer function $H_k$ can be determined for a constant cuff pressure $P_{cuff}$ or for a time-varying cuff pressure $p_{cuff}(t)$.

This makes it possible to determine the arterial pulse wave signal on the basis of the oscillating signal component $p_{osc}(t)$ from a low-pressure plateau measurement with constant cuff pressure. This determination can be made by multiplying $H_k(j\omega)$ by $P_{osc}(j\omega)$ when dimensioning the coefficients for the description of the transfer function in the frequency domain. Alternatively, a modelling of the transfer behaviour with a time-discrete differential equation system is recommended, which allows the solution directly in the time domain by way of an iterative curve fitting. In contrast to the frequency domain, the solution in the time domain allows the consideration of non-stationary and time-variant effects in the pulse wave signal.

Figure 5:
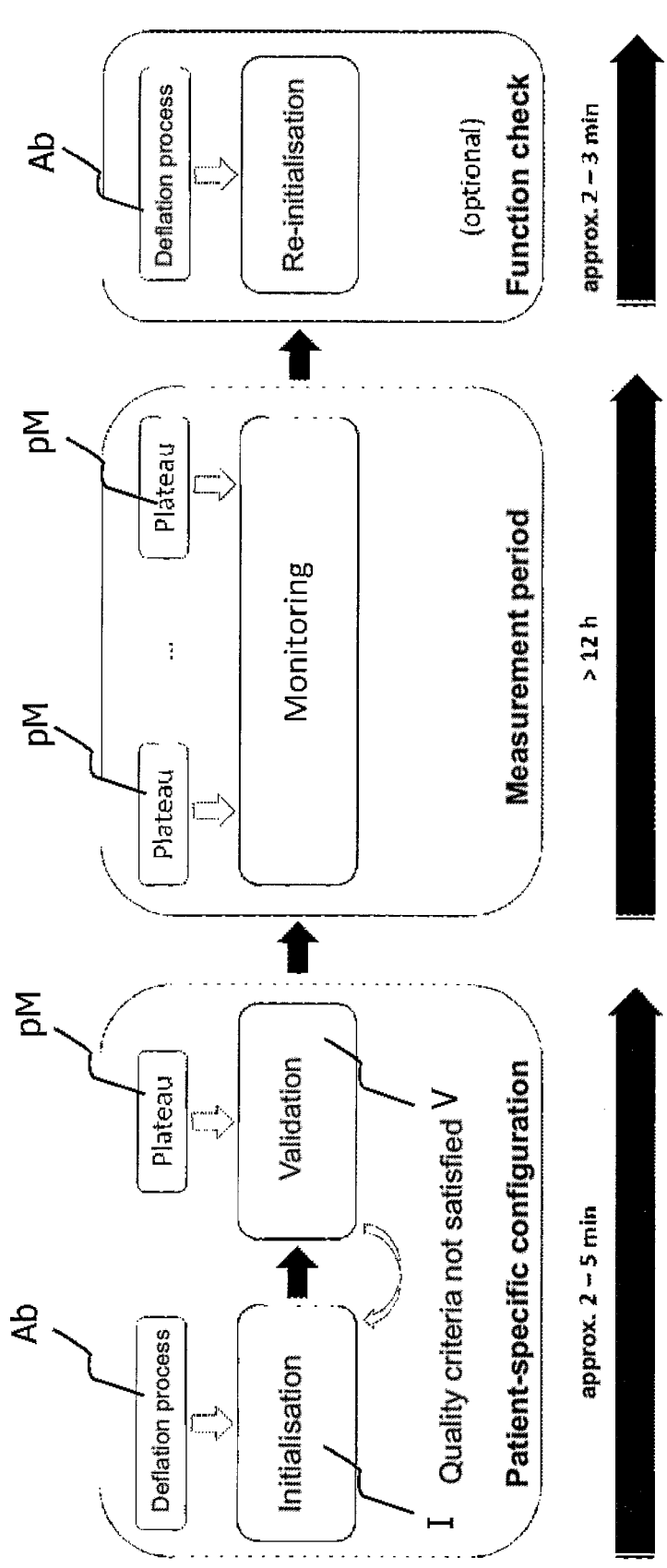
FIG. 5 shows an exemplary sequence of a 24-hour blood pressure monitoring procedure at low counter pressure with a mobile blood pressure measuring device.

FIG. 5 shows an exemplary execution of the method for determining blood pressure at low counter pressure from the initialisation of the blood pressure measuring apparatus to the first step of re-initialisation as part of a function check.

In a validation step V following initialisation I, the determined and stored coefficients are validated by reconstructing the arterial pulse wave signal and determining the blood pressure values. The aim of the validation V is a determination and/or validation of the cuff pressures for the actual low-pressure plateau measurements that are to be performed during the measurement period. Thus, validation V is intended for example to determine whether a previously defined constant counter pressure for the low-pressure plateau measurements is suitable for the patient/user, or whether this must be increased slightly in order to be able to measure a reliable pulse wave signal in the oscillating signal component of the cuff.

In the validation V, the blood pressure parameters ($P_{DIA}$, $P_{MAP}$, $P_{SYS}$) are determined from the oscillating cuff pressure $p_{osc}$ using the cuff-pressure-dependent transfer coefficients determined in the initialisation and are compared with the values determined by the blood pressure measuring device from the inflation or deflation process Au/Ab, i.e. the reference values. The validation V is successful if the blood pressure values determined with the transfer coefficients do not exceed a predefined deviation from the reference values. If the validation V is invalid, the initialisation I is repeated with a repetition of the initialisation measurement, for example the complete oscillometric measurement M. Causes for the failure of the initialisation I can be, among other things, strong disturbances of the measurement data used for the initialisation due to movement artefacts or incorrect sensor position.

A suitable adaptation of the validation step V is the substitute or additional determination of the blood pressure parameters ($P_{DIA}$, $P_{MAP}$, $P_{sys}$) on the basis of a low-pressure plateau measurement pM reconstructed from the oscillating cuff pressure $p_{osc}$. With the help of the pulse wave analysis, suitable pulse waves are extracted from the deflation process and then transformed into a virtual low-pressure plateau measurement by signal reconstruction for a counter pressure determined from the non-oscillating cuff pressure.

The validation step V can be extended by reconstructing multiple virtual low-pressure plateau measurements pM from the oscillating pressure component $p_{osc}$. For each reconstructed low-pressure plateau measurement pM, an assessment is carried out by a separate validation V according to the above-described procedure and, based on the virtual low-pressure plateau measurement with the highest quality, the measurement parameters for the low-pressure monitoring are determined and stored in a low-pressure configuration. This low-pressure configuration is in particular person-specific and individualised. Exemplary parameters that can be stored in the low-pressure configuration are the cuff pressure required for the measurement, the optimal plateau duration and the optimal number of low-pressure plateaus.

An advantageous extension of the validation V is the combination of multiple virtual low-pressure plateau measurements for simultaneous determination of the blood pressure parameters ($P_{DIA}$, $P_{MAP}$, $P_{SYS}$).

A suitable adaptation of the validation V is the substitute or additional execution of real low-pressure plateau measurements pM as well as combinations of low-pressure plateau measurements pM at either fixed or low counter pressures between 0 and 100 mmHg derived from at least one previous initialisation measurement.

After successful validation V, the initialisation result, the validation result and the parameters necessary for blood pressure monitoring are structured and stored in the external or internal control and evaluation unit 1 and/or 2. Necessary parameters are given, for example, by the specification of the measurement intervals, of the limit values for the calculation algorithms and, in particular, the low-pressure configuration. The latter defines the measurement parameters used for blood pressure measurement, such as counter pressure and plateau duration.

Blood pressure monitoring is carried out during the measurement period. One or more low-pressure plateau measurements pM is/are recorded at fixed time intervals, and the blood pressure parameters are determined with the help of the transfer coefficients determined in the initialisation.

The method can be extended to include an autonomous function check, in which a re-initialisation is carried out using a complete oscillometric measurement M and the transfer coefficients determined are compared with the transfer coefficients determined in previous initialisation or re-initialisation steps.

A useful extension of the method is the substitute or additional function check or checking of the validity of the initialisation parameters during the measurement period on the basis of the oscillating signal components of the low-pressure plateau measurements.

Use Case A2

Figure 6:
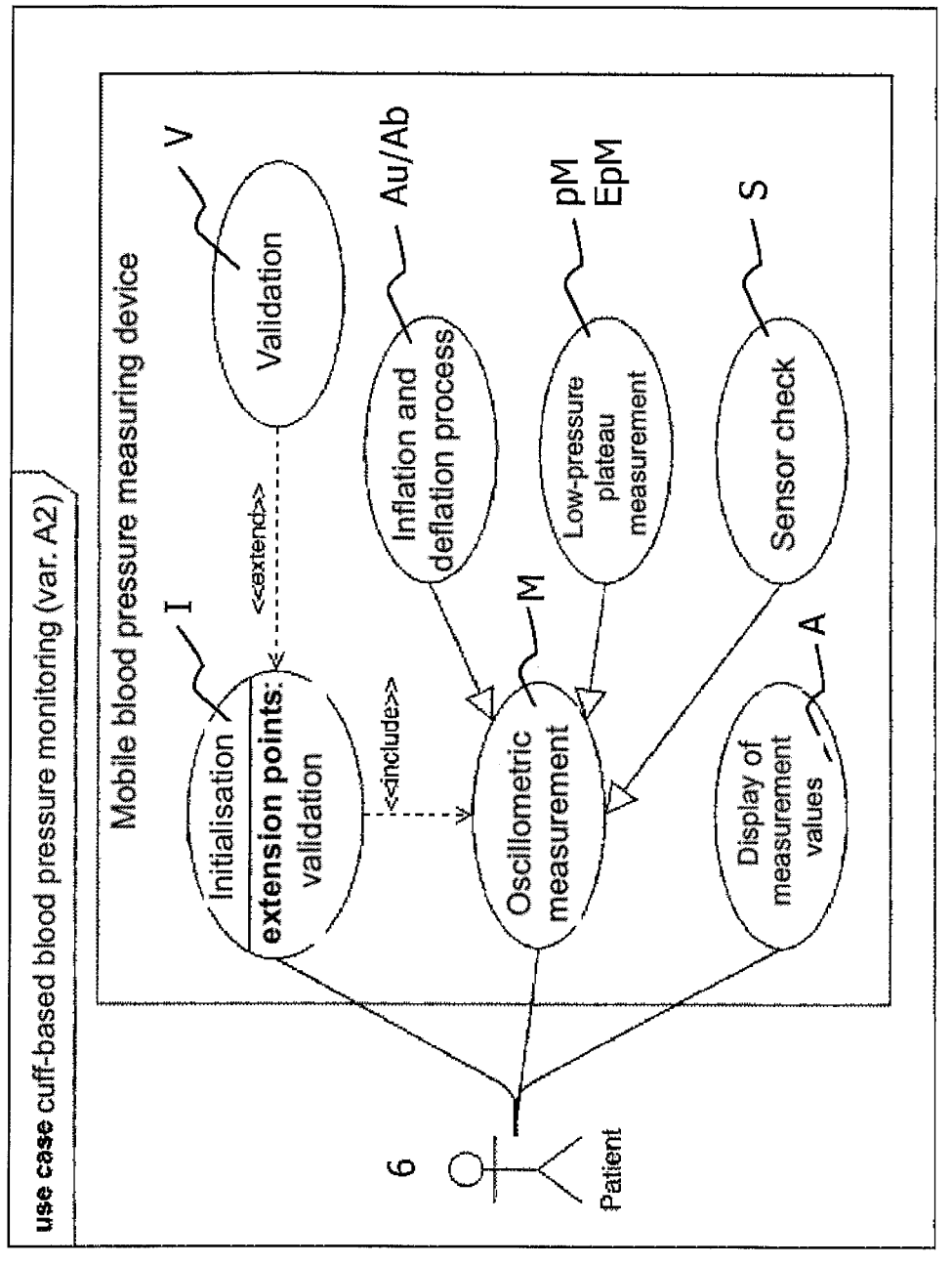
FIG. 6 shows an illustration of an exemplary use case A2.

Use case A2 shown in FIG. 6 is a useful extension of the measurement method.

In use case A2, the daily frequency of the monitoring recordings is reduced to one or two measurements, however the aim is for a longer observation period in homecare use of several days or weeks. Since continuous sensor positioning or sensor application over a longer observation period is not possible, depending on the sensor technology used, for example in the case of oscillometric measurement with a blood pressure cuff, a checking of the sensor-dependent initialisation parameters must be carried out before a low-pressure plateau measurement.

The low-pressure plateau measurements pM carried out at intervals of, for example, 8 to 10 hours are also referred to below as single-spot low-pressure plateau measurements EpM. A sensor check S is carried out before and/or during the single-spot low-pressure plateau measurement EpM.

The sensor check S allows a correction of the sensor position, for example of the cuff fit, via interaction with the user via a user interface. In addition, the sensor check S allows the adjustment of a sub-set of the transfer coefficients determined in the initialisation I, in particular the partial transfer function $H_{k,filt}$, in order to maintain the accuracy of the blood pressure determination.

The sensor check S can be exemplified by the analysis of additional multimodal sensor and actuator data which are acquired during the single-spot low-pressure plateau measurement and compared with reference and limit values determined from the initialisation (e.g. cuff volume at predefined low counter pressure). An advantageous embodiment of the method determines the correct application of the sensor on the basis of the oscillating and non-oscillating signal components extracted from a low-pressure plateau measurement. For example, evaluation parameters are extracted here from a time series analysis, spectral analysis and/or time-frequency composite representation of the components and are compared with the reference and limit values determined from the initialisation. The evaluation parameters can characterise, e.g., trends and gradients of the non-oscillating signal component as well as transient signals (jumps, artefacts) in the signal components.

An exemplary embodiment of use case A2 is to allow cuff-based low-pressure blood pressure determination in which one low-pressure plateau measurement or a combination of low-pressure plateau measurements is performed twice daily (e.g., in the morning and in the evening) after re-application of the blood pressure cuff, without the need for re-initialisation of the method.

Use Case B

Figure 7:
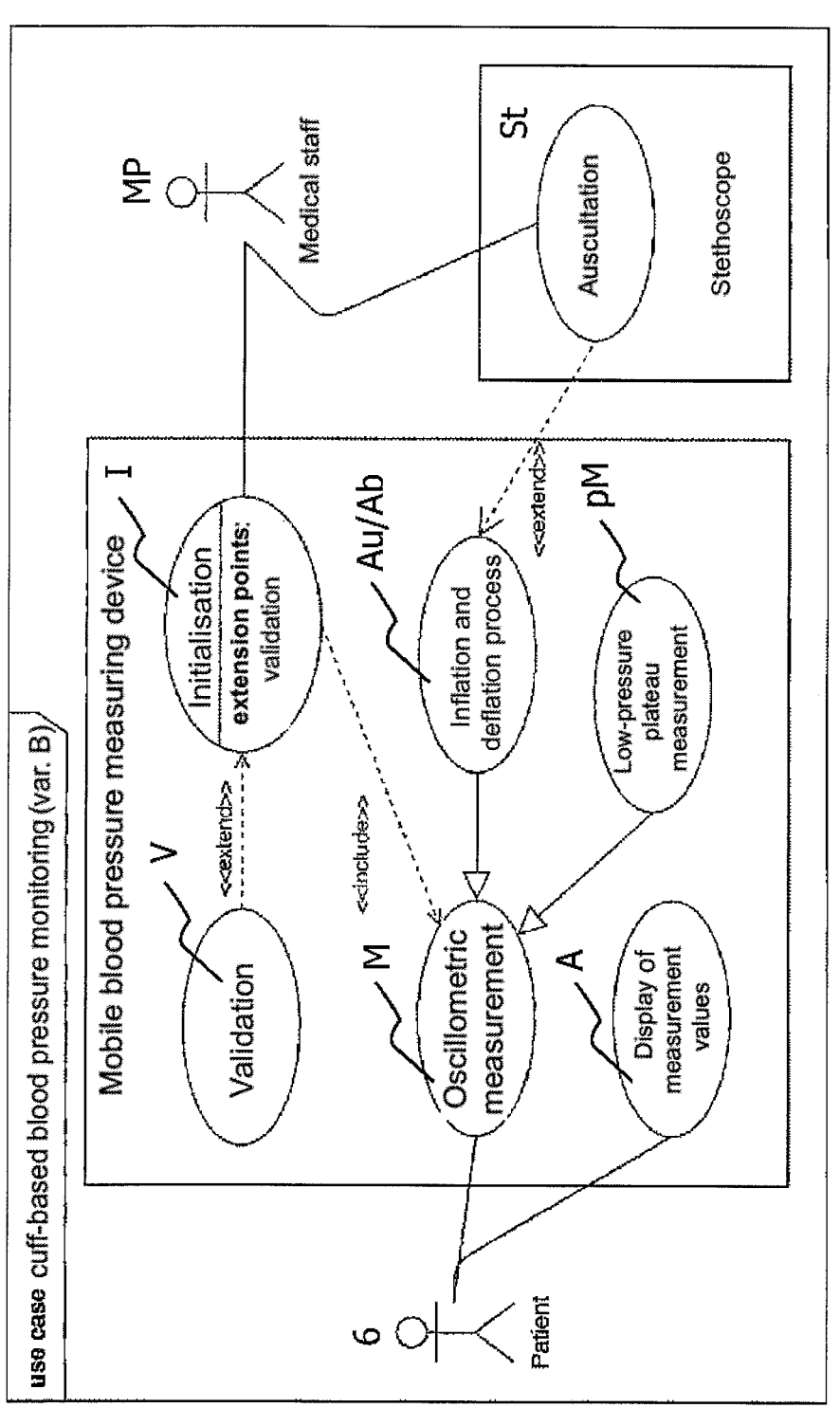
FIG. 7 shows an illustration of an exemplary use case B.

FIG. 7 shows a possible extension of use cases A1 and A2. This is referred to as use case B. In this use case, blood pressure monitoring is carried out over a narrowly limited period (e.g. 24*h* monitoring) using a professional mobile blood pressure monitor.

In use case B, the initialisation I is carried out by professional medical staff MP during a patient visit in a medical facility (e.g. a doctor's surgery). The reference values determined from an oscillometric measurement M with a cuff (e.g. $P_{DIA}$, $P_{sys}$) can be used for initialisation, or, as shown in FIG. 7, reference values determined in another way can be assigned by the medical staff. In addition, the medical staff can check and adapt the initialisation (e.g. by visual processing with a graphical user interface), can inspect the parameters determined in the initialisation, and can input additional person-specific parameters.

The reference values can be determined, e.g., by the gold standard of auscultation, Korotkoff sounds, which is accepted according to the current state of the art. The auscultation standard can be performed by the doctor themself or supported by the blood pressure measuring device, e.g. by the acoustic detection of the Korotkoff sounds with the aid of an electronic stethoscope. The initialisation I is then valid for a predefined measurement period, e.g. 24 hours. The measuring frequency is approx. every 15-30 minutes.

Use Case C1

Figure 8:
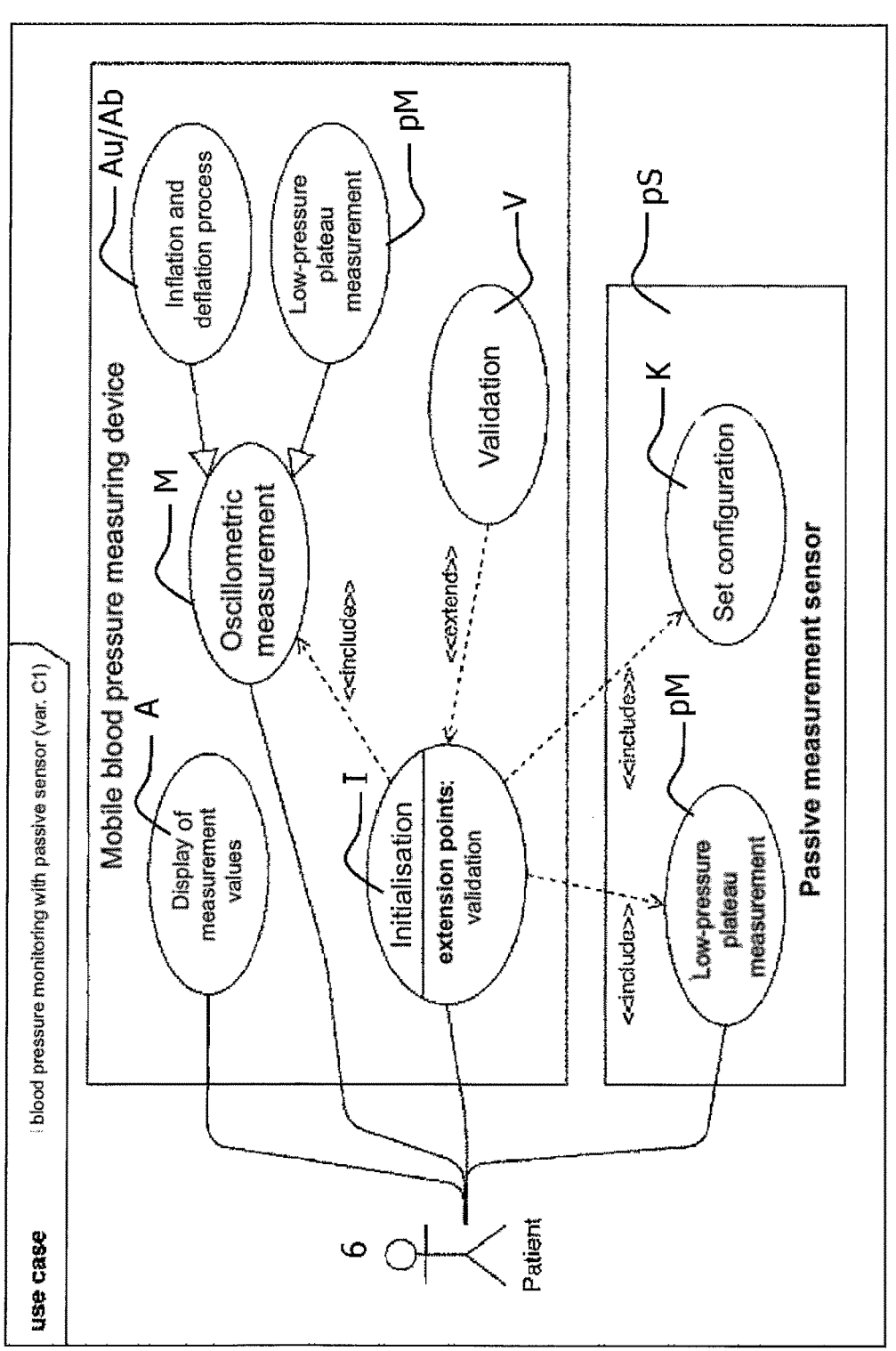
FIG. 8 shows an illustration of an exemplary use case C1.

FIG. 8 shows, by way of example, another exemplary use case C1. In this exemplary embodiment, the blood pressure measuring apparatus is supplemented by a passive measurement sensor pS, which is intended to allow a load-free blood pressure measurement during the measurement period. Passive measurement sensors in the context of the method for operating a blood pressure measuring apparatus described herein describe sensor measuring units which have no or a negligible or, to a non-variable extent, a constant effect on the patient or user. E.g., measurement units with optical sensors for the detection of a PPG according to this definition are represented by a passive measurement sensor. An electromagnetic sensor (e.g. near-field radar) for contactless pulse wave measurement can also serve as a passive sensor. In addition, a patch or textile compression stocking with integrated strain sensors without active elements to control the compression level represents a passive sensor.

Use Case C2

Figure 9:
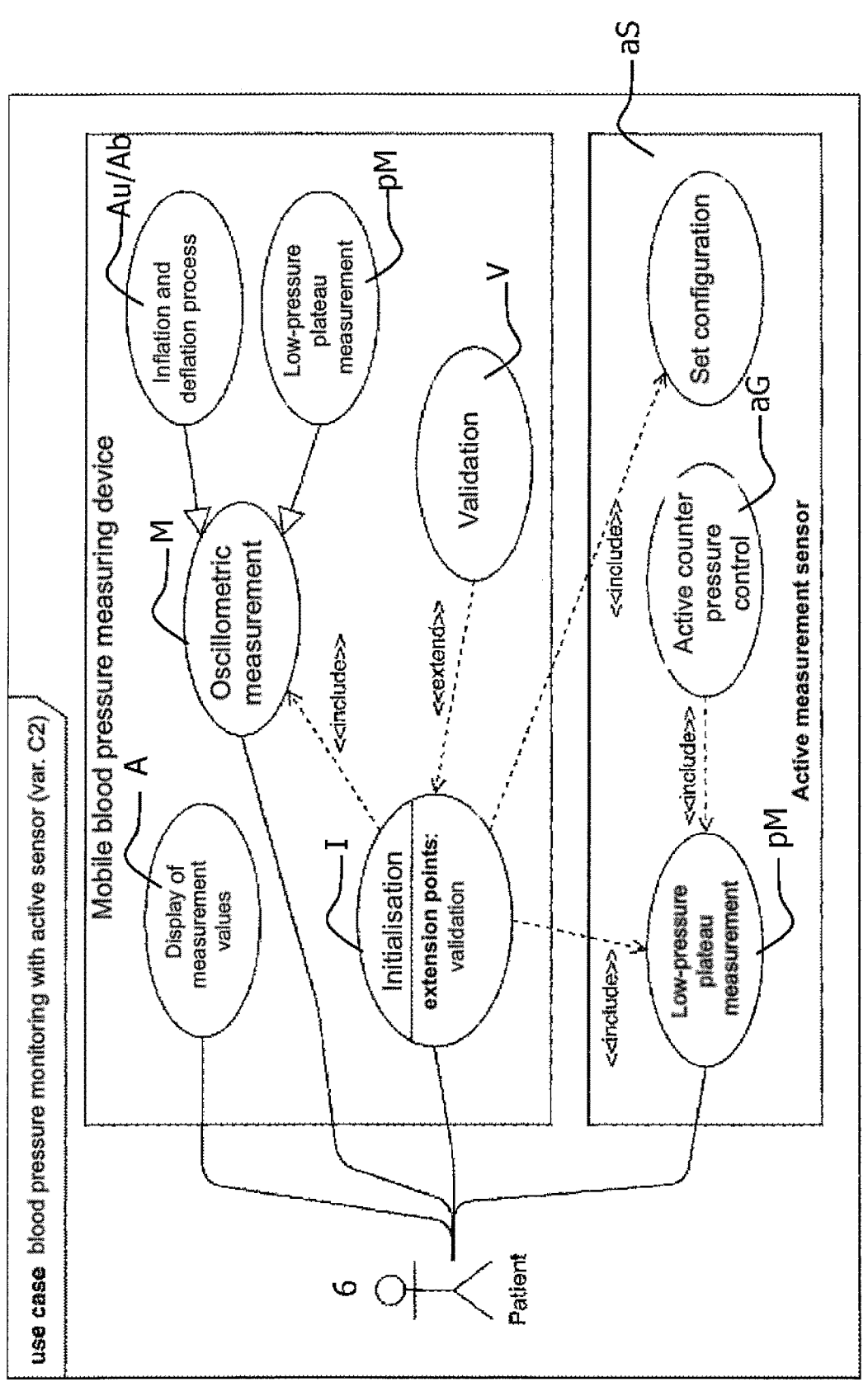
FIG. 9 shows an illustration of an exemplary use case C2.

In the exemplary use case C2 shown in FIG. 9, the blood pressure measuring apparatus is supplemented by an active measurement sensor aS. The active measurement sensor aS is initialised, for example, via an oscillometric measurement M in an initialisation I analogous to the exemplary embodiments listed above. During the low-pressure measurement pM, the contact pressure of the measuring unit, as well as the counter pressure acting from the measuring unit on the patient or user (and thus the transmural pressure prevailing in the peripheral artery) can be controlled by an active counter pressure control system aG. Possible elements of an active counter pressure control system aG are the electronics implementing the electronic control loop, an actuator (e.g. a piezoelectric element or an electromechanical apparatus) and a pressure measurement sensor, which can also be used as a measurement sensor for blood pressure measurement.

The active counter pressure control system aG can, for example, generate one or more predefined counter pressures for a tonometric sensor head. Another example of an active counter pressure control system is the embedding of electromechanical actuators in a textile measuring stocking, which changes its longitudinal deflection depending on an electrical, time-variable or constant voltage and thus leads to a change in the diameter of the textile measuring stocking. The change in the diameter of the textile measuring stocking in turn causes a change in the counter pressure acting on the artery and thus in the transmural pressure.

The active counter pressure control system allows the active measurement sensor connected to the blood pressure measuring device to perform low-pressure plateau measurements pM with different constant counter pressures. For example, a sequence of low-pressure plateau measurements can be processed during a measurement process, in which a low-pressure plateau measurement with a constant counter pressure of 50 mmHg is applied to the patient/user, followed by a low-pressure plateau measurement with a constant counter pressure of 70 mmHg.

Use Case D

A possible combination of use cases B and C1 and/or C2 is represented by an exemplary use case D, not shown here in the figures, in which the blood pressure monitoring with low-pressure plateau measurements is carried out during an inpatient stay of the patient in a medical facility, e.g. a hospital. Patients in inpatient and/or intensive care treatment represent a particularly vulnerable patient group, for whom continuous monitoring of as many relevant, in particular cardiovascular, vital parameters as possible is necessary on the one hand. On the other hand, the load on the patient and the effort for the medical staff must be kept as low as possible.

An exemplary embodiment according to use case D is the initialisation of a blood pressure measuring apparatus with a reference measurement, e.g. an invasive blood pressure and pulse wave measurement by means of an arterial catheter during a routine diagnostic or therapy procedure. With the help of the arterial pulse wave recording determined from the invasive reference measurement and the low-pressure plateau measurement recorded with the non-invasive blood pressure measuring apparatus (e.g. by an oscillometric measurement, optical measurement, etc.), the person-specific transfer behaviour from the artery to the non-invasive measurement sensor can be determined within the scope of the initialisation. Afterwards, a low-load blood pressure measurement is possible during the inpatient monitoring of the patient with a single low-pressure plateau measurement or a combination of low-pressure plateau measurements.

In the following, exemplary details of the initialisation steps and the signal processing that takes place during this process, as well as the blood pressure measurements and the low-pressure blood pressure measurement and the signal processing that takes place during this process will be explained in greater detail. For the execution of the method steps described below, the configuration shown by way of example in FIG. 1 and explained above is used. If deviations from this are necessary, this will be mentioned below.

Figure 10:
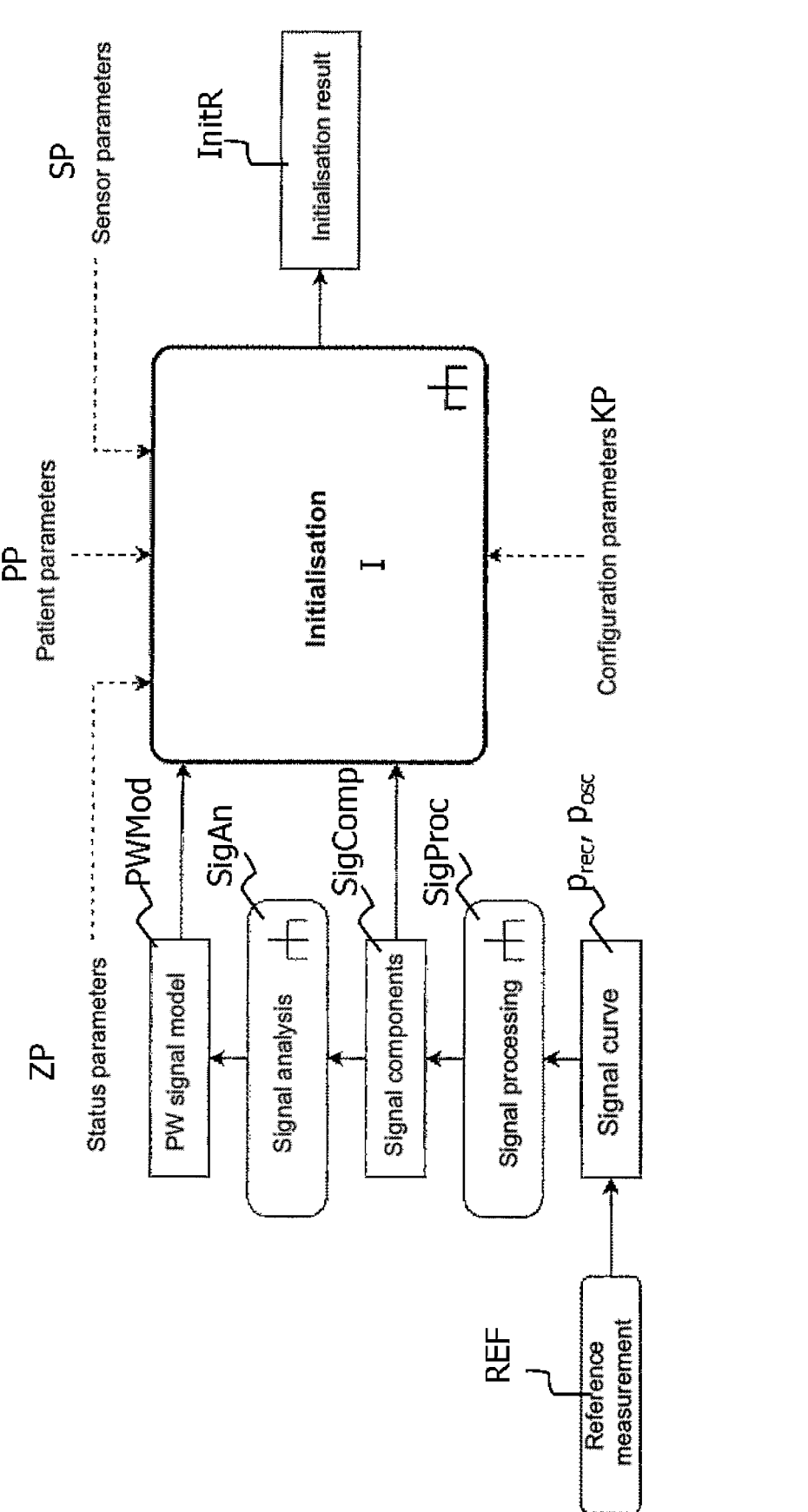
FIG. 10 shows exemplary interfaces of the initialisation of the method and necessary pre-processing steps before initialisation.

As shown in the exemplary measurement sequence in FIG. 5, an initialisation I of the method takes place at the start of a given measurement period, followed by a validation V of the initialisation result. The initialisation I of the method is shown in FIG. 10. This is the main component of a person-specific configuration of a blood pressure measuring apparatus according to FIG. 1 for carrying out a blood pressure measurement using low-pressure plateau measurements.

In a reference measurement REF, the registering and storing of a referential temporal signal curve $p_{rec}$ of a pulsating signal takes place, e.g. the direct detection of the pulse wave via an invasive blood pressure measurement or the detection of the oscillating signal component $p_{osc}$ of an oscillometric measurement by means of a blood pressure cuff.

If not otherwise available, the blood pressure values of the patient or user prevailing at the time of the reference measurement can be determined from the reference measurement REF and transferred to the initialisation.

Possible reference signals for initialisation can be, in particular:

Measurement data ($p_{osc}$, $p_{cuff}$) from a complete or partial deflation process Ab of an oscillometric measurement according to the preceding use examples.

Measurement data ($p_{osc}$, $P_{cuff}$) from an inflation and/or deflation process Au/Ab of an oscillometric measurement according to the preceding use examples.

Measurement data ($p_{osc}$, $p_{cuff}$) from a complete/partial inflation process Au of an oscillometric measurement according to the preceding use examples.

Measurement data ($p_{osc}$, $p_{cuff}$) from at least one, preferably N, plateau measurements pM at N different, constant counter pressures with constant patient position/posture according to the preceding use examples.

Measurement data ($p_{osc}$, $p_{cuff}$) from at least two, preferably N, plateau measurements pM with M N (possibly different) but constant counter pressures according to the preceding use examples, but with different patient positions or patient postures (i.e. when performing different manoeuvres before or during the blood pressure reference measurement that lead to a change in the arterial blood pressure).

Measurement data ($p_{osc}$, $p_{cuff}$) for a plateau measurement pM with low but time-variable counter pressure.

It is also possible to use measurement data ($p_{invasive}$) from an invasive pulse wave and blood pressure measurement with a catheter in conjunction with a simultaneous or near real-time oscillometric measurement in one of the above-mentioned embodiments and use cases.

After the reference measurement REF, a signal processing SigProc takes place, which extracts relevant signal components SigComp for the subsequent pre-processing steps and the initialisation I from the signal curve.

Using the signal components SigComp, a detailed signal analysis SigAn is carried out for the extraction of pulse wave features and the formation of a pulse wave signal model PWMod.

Necessary input variables for the initialisation process of the method are the signal components SigComp and the PW signal model PWMod extracted from the signal curve. Optional interfaces provide the transfer of input variables to the initialisation, which describe status parameters ZP of the blood pressure apparatus and the method, sensor parameters SP, configuration parameters KP and patient parameters PP.

Status parameters ZP describe, for example, the time of the initialisation, previous initialisations and their results, the status of the blood pressure measuring apparatus or the status of the method.

Sensor parameters SP describe, for example, the type of sensor (pressure sensor, mechanical sensor, electromechanical sensor, optical sensor, electromagnetic sensor), the type of measuring unit (e.g. passive, active), the size and characteristics of the sensor (e.g. measuring position, cuff size, wavelengths, weight, etc.).

Patient parameters PP describe, for example, the age, body weight, height, gender and status of the patient or user.

Configuration parameters KP define, for example, the description type of the transfer behaviour as well as the domain of the description/calculation of the transfer behaviour (e.g. time domain, frequency domain, time-frequency domain), the selected modelling approach, the underlying model type, the optimisation algorithm used, and definition and value ranges.

The initialisation I of the method provides an initialisation result InitR, which contains, among other things, the coefficients of the sought, person-specific transfer behaviour with quality parameters and parameters for describing the initialisation process (e.g. duration of the initialisation, iteration steps, status of the initialisation).

Figure 11:
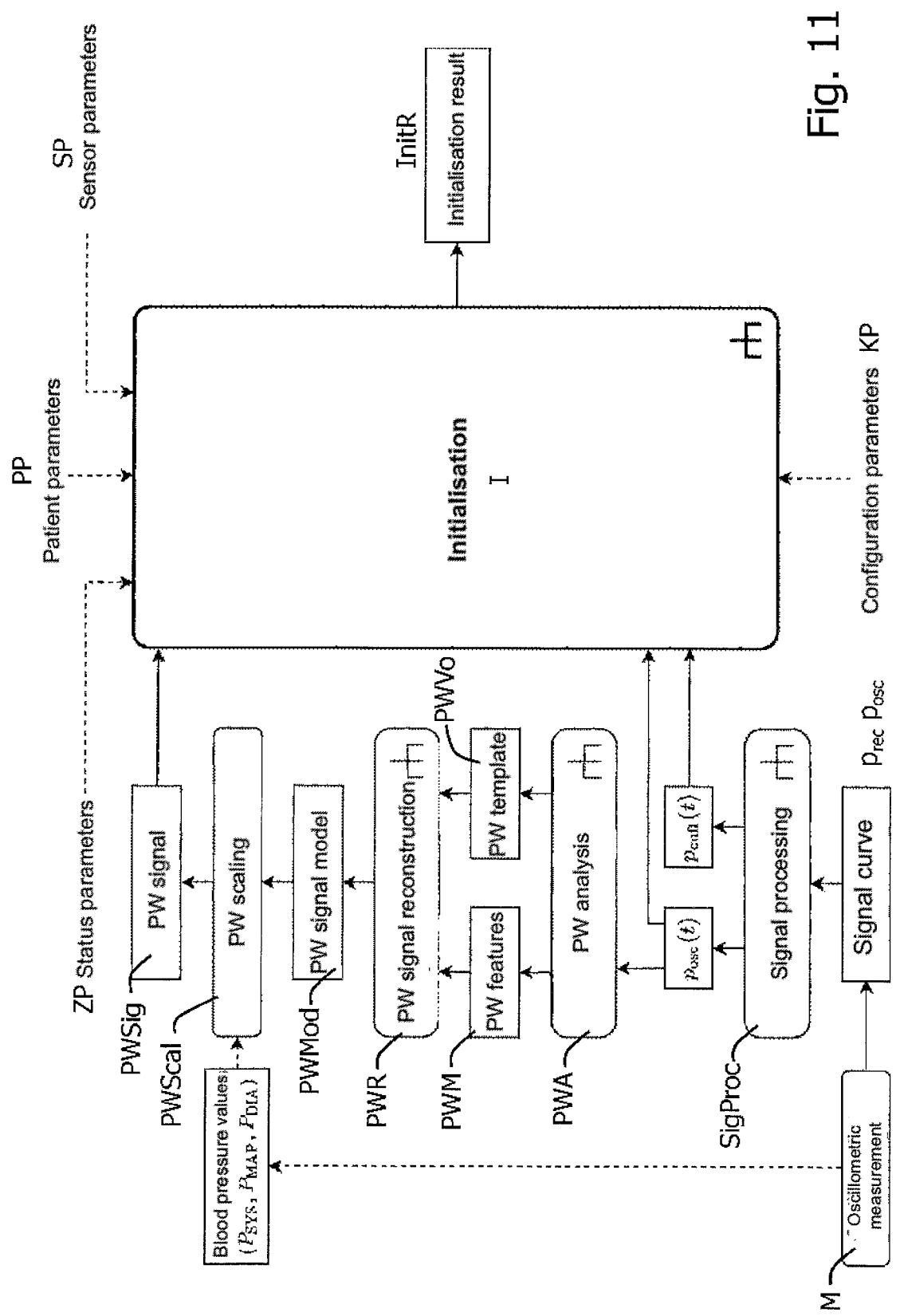
FIG. 11 shows a detailed illustration of exemplary interfaces of the initialisation of the method and necessary pre-processing steps before initialisation when using an oscillometric measurement for initialisation.

FIG. 11 shows exemplary interfaces of the method step of initialisation I with pre-processing steps and data objects for an exemplary embodiment of the presented method when using an oscillometric measurement with evaluation of the deflation process. The predefined peak pressure may be higher here than the expected systolic blood pressure during the reference measurement. However, the predefined peak pressure can also be far below the expected systolic blood pressure (in the case of a low-pressure deflation process with partial inflation process).

If no complete oscillometric measurement is performed, the reference parameters can be determined from other measurements, in particular via a catheter sensor, or from the history of previous measurements. An extension is the determination of reference parameters from a classification of pulse waves and an assignment of pulse wave features via an empirical equation of an associated sub-population.

On the basis of the oscillometric measurement M, the signal curve of the pressure measurement sensor ($p_{rec}$) is determined. In addition, the blood pressure values for the systolic ($P_{SYS}$), the diastolic ($P_{DIA}$) and the mean arterial ($P_{MAP}$) blood pressure are determined as reference values (for example from the deflation process).

In the signal processing SigProc, the time curves of the oscillating ($p_{osc}$) and non-oscillating ($p_{cuff}$) signal components are determined and serve as input variables for the initialisation.

Using the oscillating signal component $p_{osc}$, a pulse wave analysis PWA is then carried out, from which the pulse wave features PWM and a pulse wave template PWVo result. In a pulse wave signal reconstruction PWR, a pulse wave signal model PWMod is calculated from the PW template using the PW features of $p_{osc}$. Using the blood pressure values known from the reference measurement, the PW signal model is scaled and, if necessary, transformed in a pulse wave scaling PWScal, so that the resulting calculated PW signal approximates the arterial pulse wave as accurately as possible.

There is a transfer of $p_{osc}$, $p_{uff}$, PW signal PWSig, status parameters ZP, patient parameters PP, sensor parameters SP and configuration parameters KP to the process of initialisation I, and the initialisation result is determined by solving an optimisation problem which maps a calculated response $p'_{osc}$ as accurately as possible to $p_{osc}$, i.e. the calculated coefficients for modelling the transfer behaviour map the PW signal as accurately as possible to $p_{osc}$.

Figure 12:
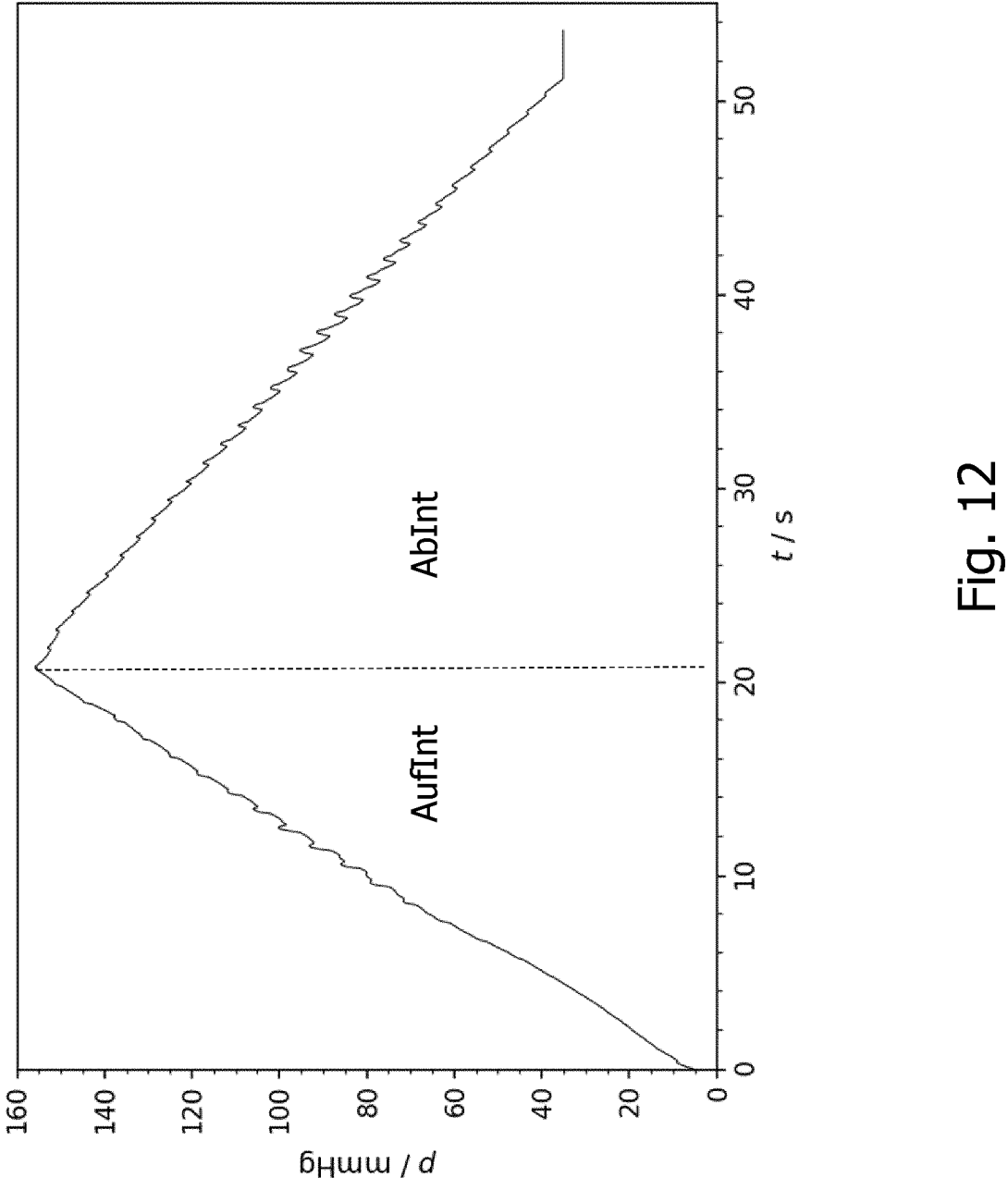
FIG. 12 shows an exemplary oscillometric measurement with blood pressure cuff with complete inflation process above the expected systolic blood pressure followed by a deflation process as a reference measurement for initialisation.

An exemplary oscillometric measurement signal is shown in FIG. 12. In the exemplary embodiment according to FIG. 11, the oscillometric measurement signal is preprocessed with the following steps:

If necessary, the sampling rate is first increased by means of an interpolation, preferably a cubic interpolation.

This is followed by a separation into oscillating and non-oscillating signal components ($p_{osc}$, $p_{cuff}$). In the example from FIG. 12, the oscillating signal component is noticeable as a jagged structure, which is superimposed on the smooth triangular curve of the pressure during inflation and deflation process.

Figure 13:
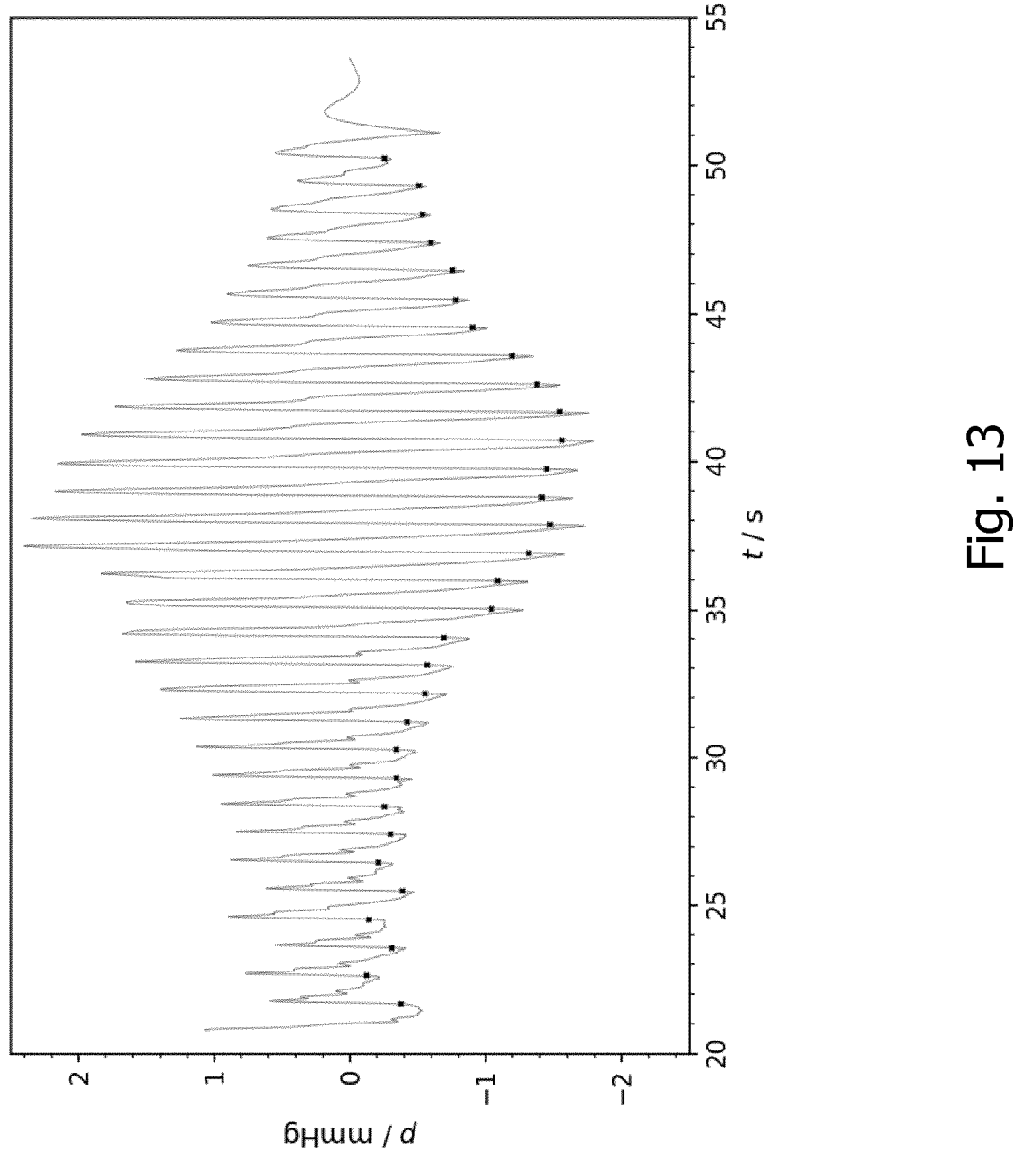
FIG. 13 shows an oscillating signal component $p_{osc}(t)$ from a complete deflation process of an oscillometric measurement.

The interval of the non-oscillating signal component is then determined, namely into an inflation interval AufInt, a deflation interval AbInt, and, if necessary, into an interval with constant counter pressure. FIG. 13 shows an example of the oscillating signal component $p_{osc}$, which has been separated from the deflation interval.

In the signal processing SigProc, after the above-mentioned pre-processing steps, an artefact detection is carried out in the non-oscillating and oscillating signal components. This involves the identification and classification of artefacts in the measurement signal as well as their occurrence times or intervals. This sub-step serves as a basis for excluding and reducing the artefacts by suitable signal-processing methods (e.g. filtering, signal decomposition with multivariate statistics, signal manipulation, etc.). The artefact detection also allows the definition of artefact-free time intervals, or so-called regions of interest (ROIs), which allow an error-corrected initialisation and model-based blood pressure determination.

Optionally, a signal portion suitable for initialisation and/or model-based blood pressure determination can be extracted from the artefact-corrected reference signal. This signal portion can contain, for example, 1 to N consecutive pulse waves.

Figure 14:
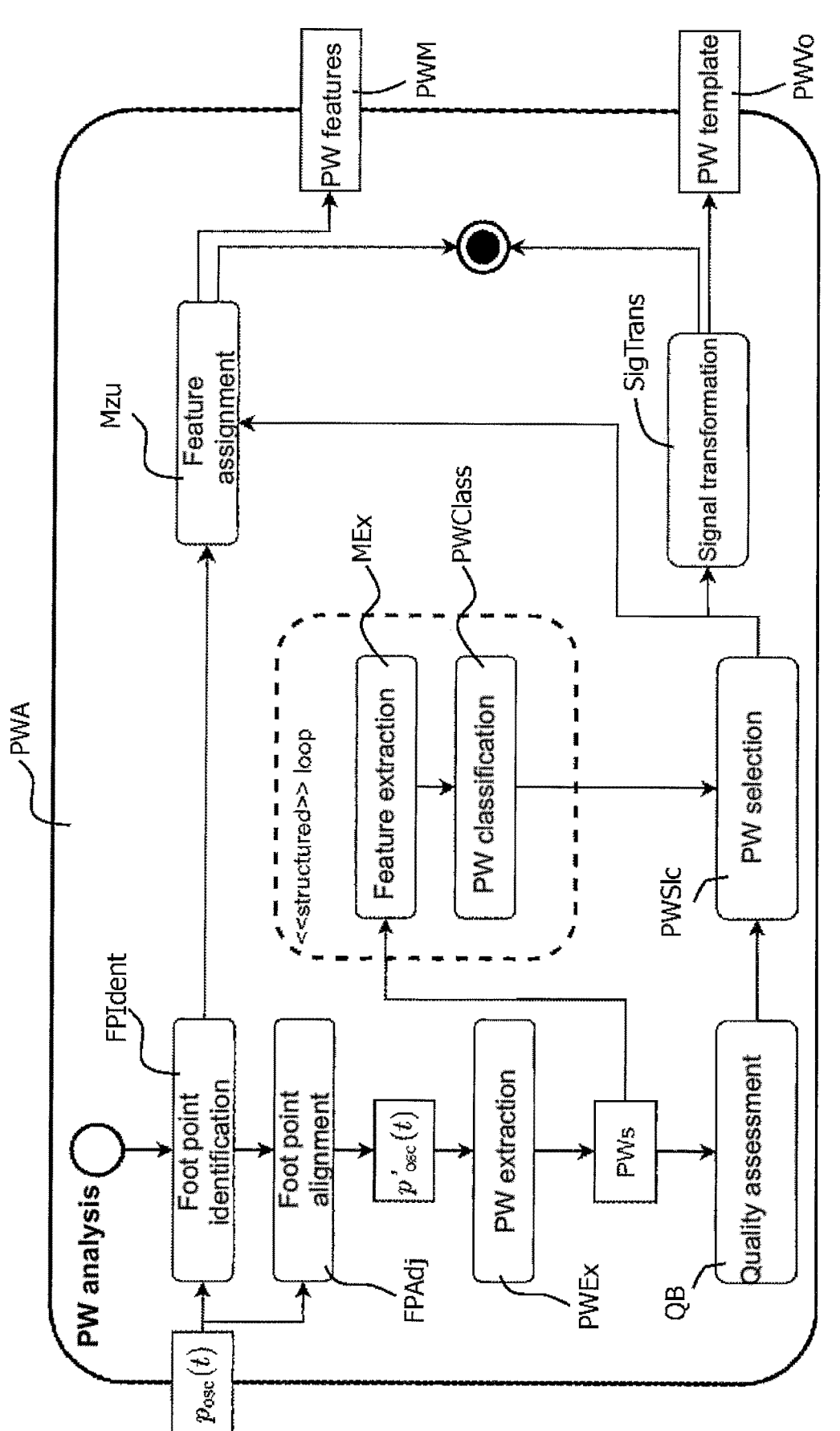
FIG. 14 shows a sequence of the pulse wave analysis for extraction of pulse wave features and for determination of a person-specific pulse wave template (PW template)

In the pulse wave analysis PWA shown by way of example in FIG. 14, pulse wave features PWM and a pulse wave template PWVo are determined from the oscillating signal component of the cuff measurement.

The aim of the PW template is to provide a precise reproduction of an averaged arterial pulse wave form in the peripheral artery (e.g. in the *A. brachialis*). In the PW analysis, a set of pulse waves (but at least one pulse wave) is extracted here from the input signal for initialisation and, after classifying the pulse waves, a pulse wave template is created from this by means of a suitable signal transformation. The steps listed below are carried out during this process.

Figure 15:
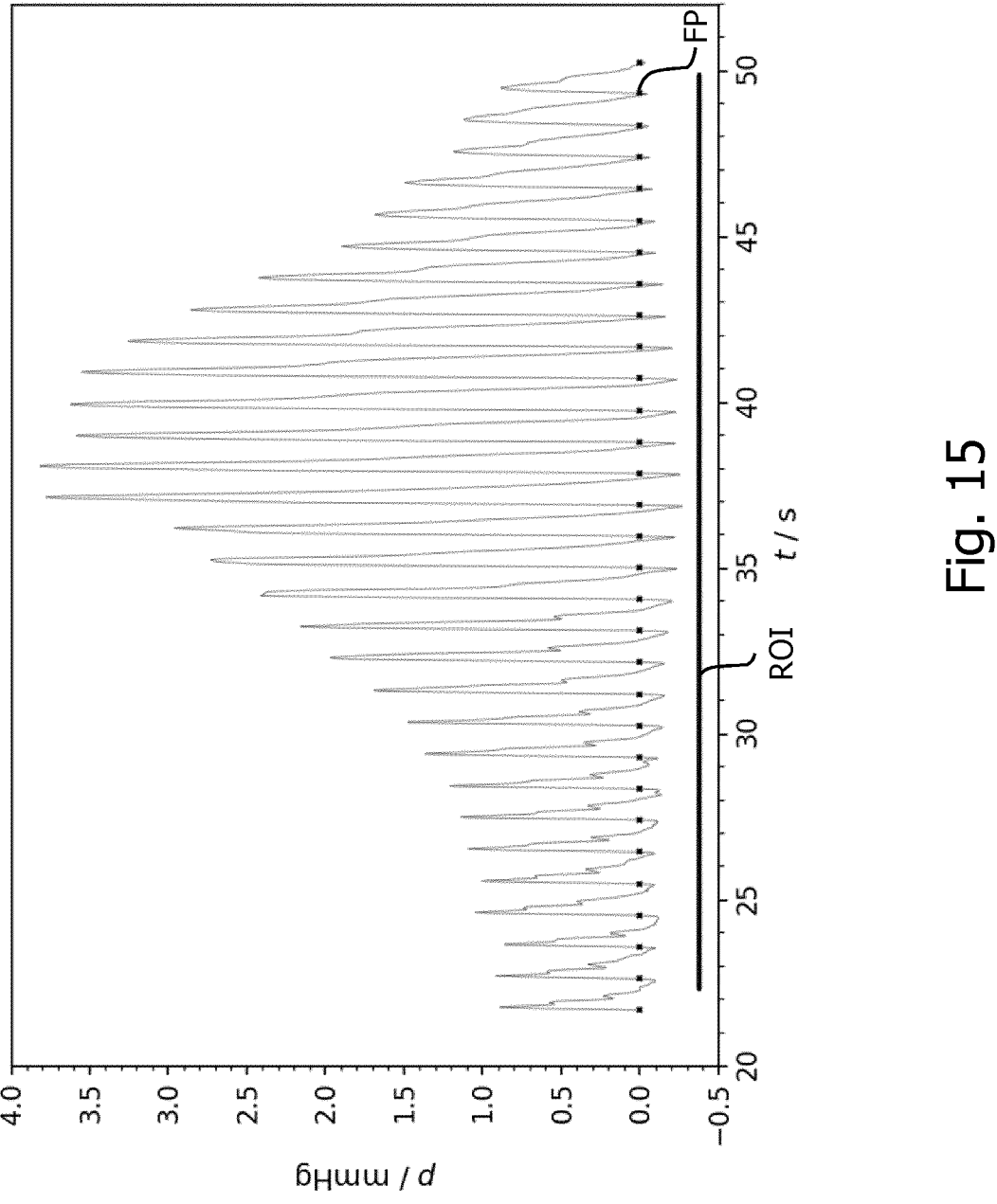
FIG. 15 shows an oscillating signal component $p_{osc}(t)$ aligned with the pulse wave foot points for the example from FIG. 12.

The oscillating signal component is segmented into individual pulse waves and the associated pulse wave foot points FP are determined. Subsequently, the oscillating signal component is aligned with the foot points by interpolation. An example of this is shown in FIG. 15. Here, the oscillating signal component $p_{osc}$ for the example from FIG. 13 is aligned with the pulse wave foot points FP. The black baselines represent exemplary markings of artefact-free evaluation areas or regions of interest (ROIs). For this purpose, an artefact detection is first carried out taking into account the non-oscillating signal component.

The aligned, oscillating signal component is decomposed into data over individual periods to identify individual pulse waves.

Subsequently, a classification and quality assessment of the individual pulse waves is performed on the basis of the pulse wave morphology and the individual pulse wave features. Based on the classification result, a sub-set of extracted pulse waves is formed.

The classification can be performed on the basis of the pulse wave morphology, the pulse wave features or pre-defined measurement parameters. A suitable combination of classification rules is possible and advantageous. For example, pulse waves only from the supra-systolic range $P_{cuff} > P_{SYS}$ that have the same or similar pulse wave form are taken into account.

The pulse wave analysis according to FIG. 14 starts with a reading-in of the oscillating signal component $p_{osc}(t)$. A foot point identification FPIdent is then carried out. In a feature assignment MZu, a classification is assigned to the individual pulse waves detected via the foot points thus determined.

The identified foot points are aligned via a foot point alignment FPAdj and substantially normalised to a specific signal offset. This means, above all, the alignment to a predefined zero line.

This results in an aligned oscillating signal component $p'_{osc}(t)$. The pulse wave extraction PWEx is performed on this aligned oscillating signal component.

The extracted pulse waves PW are qualitatively assessed in a quality assessment QB; this concerns in particular the selection of artefact-laden signal curves and the selection of pulse waves in certain pressure ranges during the deflation process or certain pulse wave forms.

In conjunction with this, a feature extraction MEx is carried out on the individual pulse waves, and a pulse wave classification PWClas is carried out. The steps QB, MEx and PWClas result in a pulse wave selection PWSlc, which forms the basis for the feature assignment step MZu.

Starting from the pulse wave selection PWSlc, a signal transformation SigTrans takes place to obtain a pulse wave template PWVo.

The signal transformation SigTrans takes into account a varying haemodynamic (e.g. due to a change in heart rate) by means of suitable operations (e.g. dynamic time warping, non-linear/linear scaling, interpolation, digital filtering). In addition, the amplitude of the individual pulse waves is normalised. The extracted pulse waves can enter the signal transformation SigTrans with different weighting.

A possible example of a simple signal transformation is the weighted averaging of pulse waves aligned with each other using non-linear scaling operations. Conceivable alternative signal transformations can be achieved by function approximation with neural networks (or other machine learning methods), FIR filter banks, wavelet decompositions and/or signal decomposition with multivariate statistics methods (SVD, PCA, ICA).

An identification of suitable pulse wave features for the PW template is performed in order to be able to perform a PW signal reconstruction in the next step. Furthermore, the identified pulse wave features can be used to classify the patient/user and/or their status in order to select and/or generate person-specific algorithms and/or parameters based on the classification result in subsequent steps.

Figure 16:
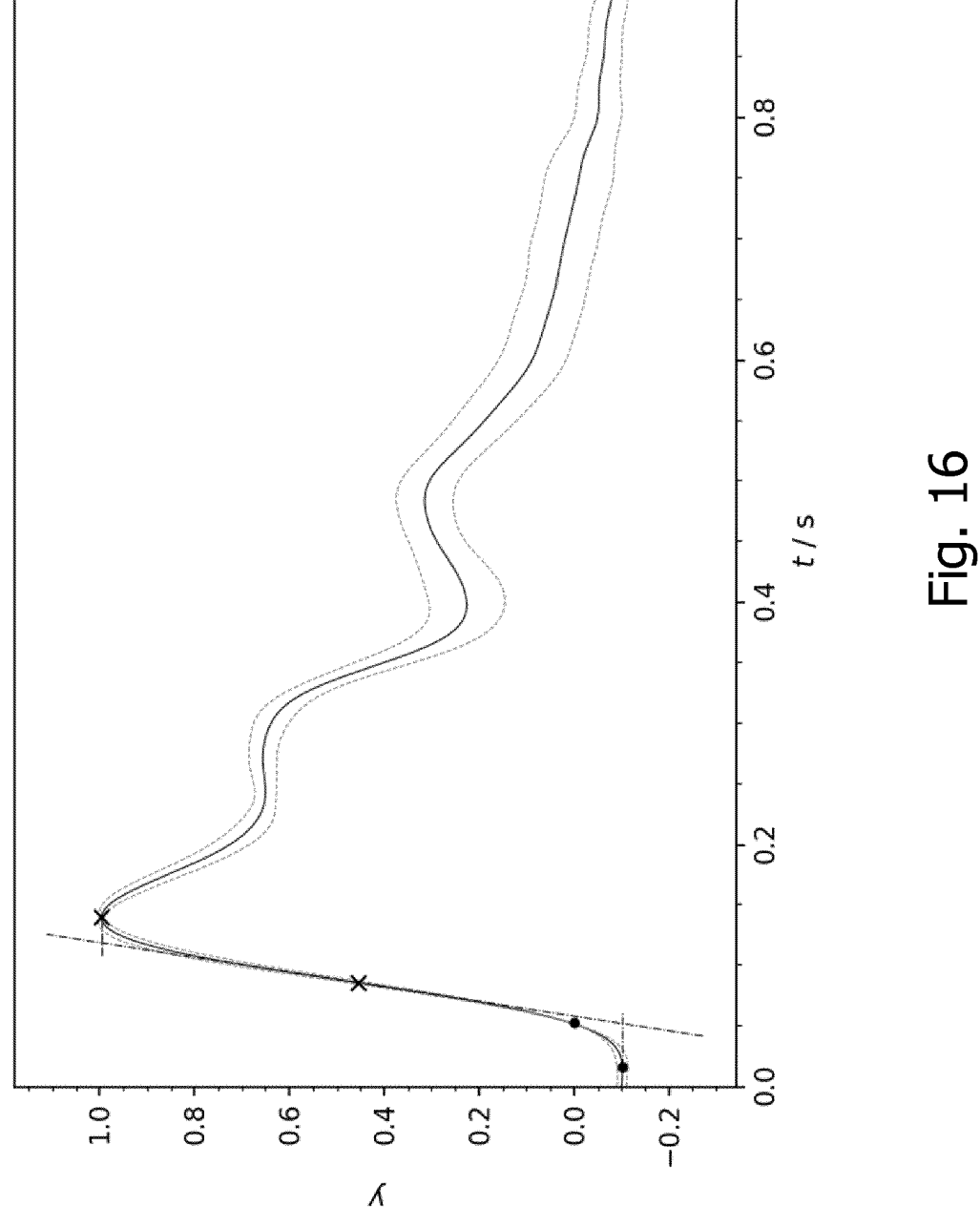
FIG. 16 shows a pulse wave template with exemplary pulse wave features resulting from the tangent intersection method (dashed lines)

FIG. 16 shows, as a continuous line, a pulse wave template (black) with exemplary pulse wave features (markings in the form of crosses and dots) resulting from a tangent intersection method (dashed lines). The dotted lines represent uncertainty ranges derived from the individual pulse waves used for the PW template, for example from a (weighted) standard deviation.

Figure 17:
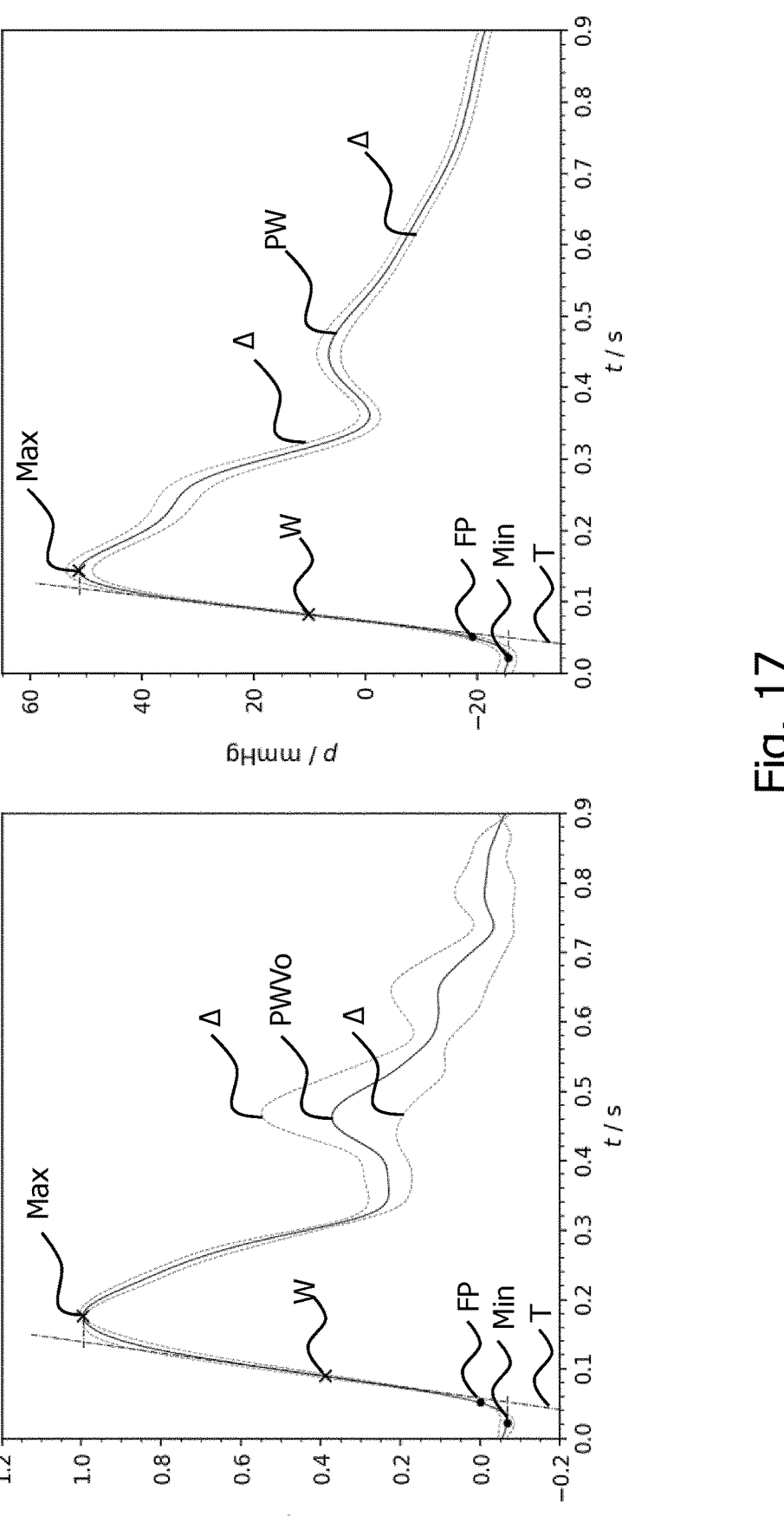
FIG. 17 shows an example of a pulse wave template determined from the supra-systolic range of the oscillometric signal component of a cuff measurement (left), right: mean-value-adjusted, averaged pulse wave of an invasive blood pressure measurement using a catheter from the *A. brachialis* in the same patient, opposite arm.

FIG. 17 shows on the left an example of a pulse wave template PWVo determined from the supra-systolic range of the oscillometric signal component with a cuff measurement. On the right is a mean-value-adjusted, averaged pulse wave PW of an invasive blood pressure measurement using a catheter from the *A. brachialis* in the same patient, opposite arm.

The example shows a case in which the PW features and PW shape between PW template and invasive pulse wave show good agreement.

The corresponding confidence ranges A are shown. The matching parameters of both curves are particularly evident in the agreement of the shapes within the present time domain as well as the temporal position of individual curve points, for example the maxima Max, inflection points W, foot points FP, minima Min, as well as tangent curves T.

Figure 18:
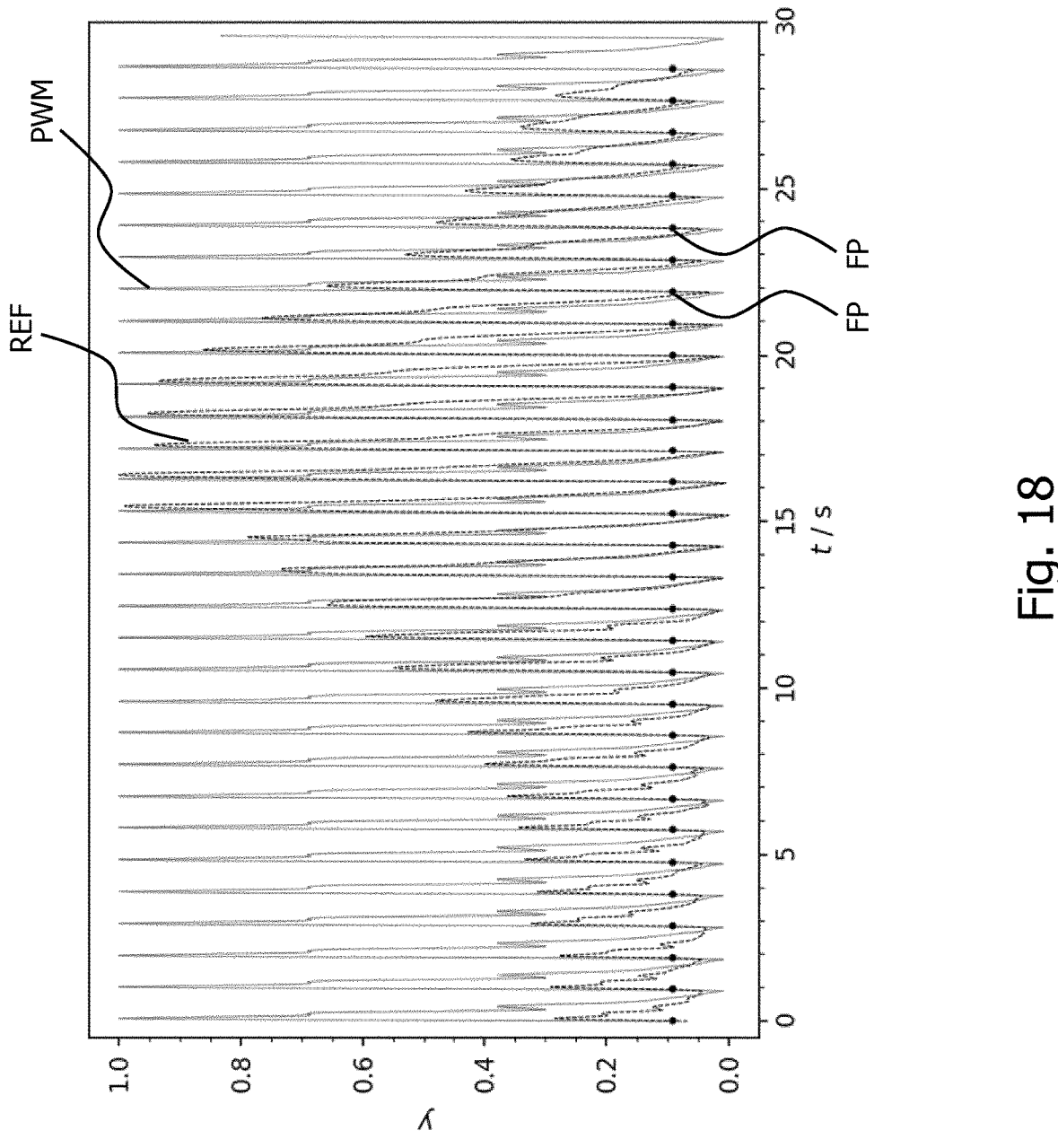
FIG. 18 shows an example of a pulse wave signal model reconstructed from concatenated and scaled PW templates (PW signal model)
Figure 19:
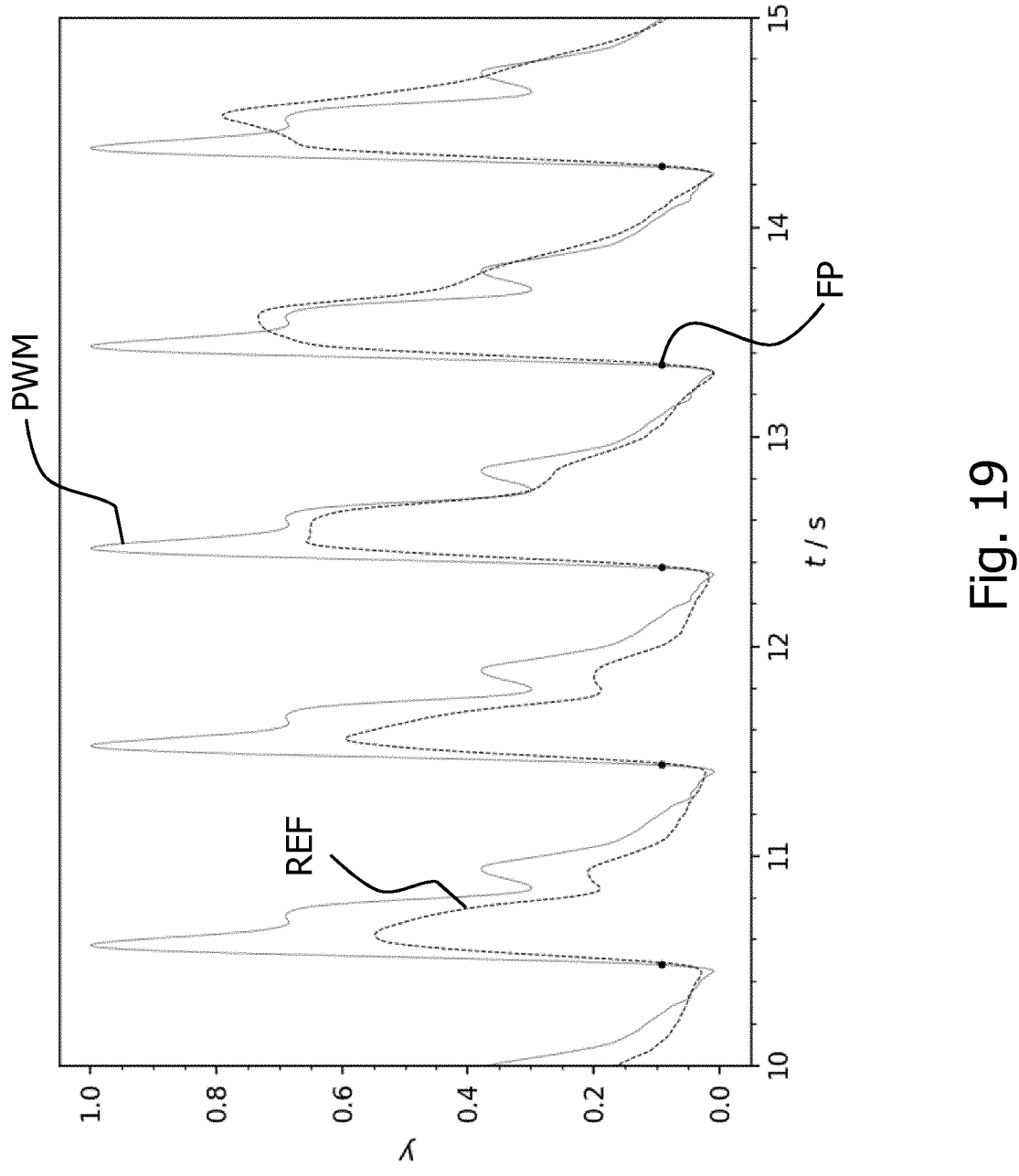
FIG. 19 shows a detail from FIG. 18.

On the basis of pulse wave features determined from the reference signal (e.g. time of the pulse wave foot points determined with the tangent intersection method), a reconstruction of a pulse wave signal model PWM time-synchronous to the oscillating signal component of the reference signal is carried out, according to FIGS. 18 and 19.

For this purpose, scaling factors and pulse wave distances are determined from the time curve of the reference signal (in particular the times of suitable pulse wave features, for example pulse wave minima, foot points FP, pulse wave maxima). Using these, a pulse wave model that is time-synchronous to the reference signal is created from the pulse wave template by interpolation (and extrapolation if necessary).

By selecting the PW template, a person-specific and class-specific PW signal model is formed, which takes into account both concrete properties from the oscillating signal component detected by the patient or user, and parameters from a database as a result of the classification result of the pulse wave features and pulse wave form in combination with person-specific and/or sensor-specific parameters (e.g. gender, age of the patient/user).

A concatenation of scaled pulse wave templates is then performed in conjunction with a cubic interpolation to avoid signal jumps and other discontinuity points. The time-variant periodicity of the detected pulse wave is taken into account here, e.g. as a result of a temporal change in the heart rate, and is included in the reconstruction of the PW signal model by scaling the PW template along the time axis.

FIG. 18 shows a PW signal model PWM which is reconstructed from concatenated and scaled PW templates and which takes into account the time-variant haemodynamics of the reference signal (black dashed line) at detected foot points FP. FIG. 19 shows a detail from FIG. 18.

From the reconstructed PW signal model, an approximated pulse wave signal axPW is determined on the basis of the blood pressure values derived from the reference measurement or the values specified by the medical staff and approximates the arterial pulse wave as accurately as possible. This can be achieved by a suitable signal transformation, for example a simple scaling.

Figure 20:
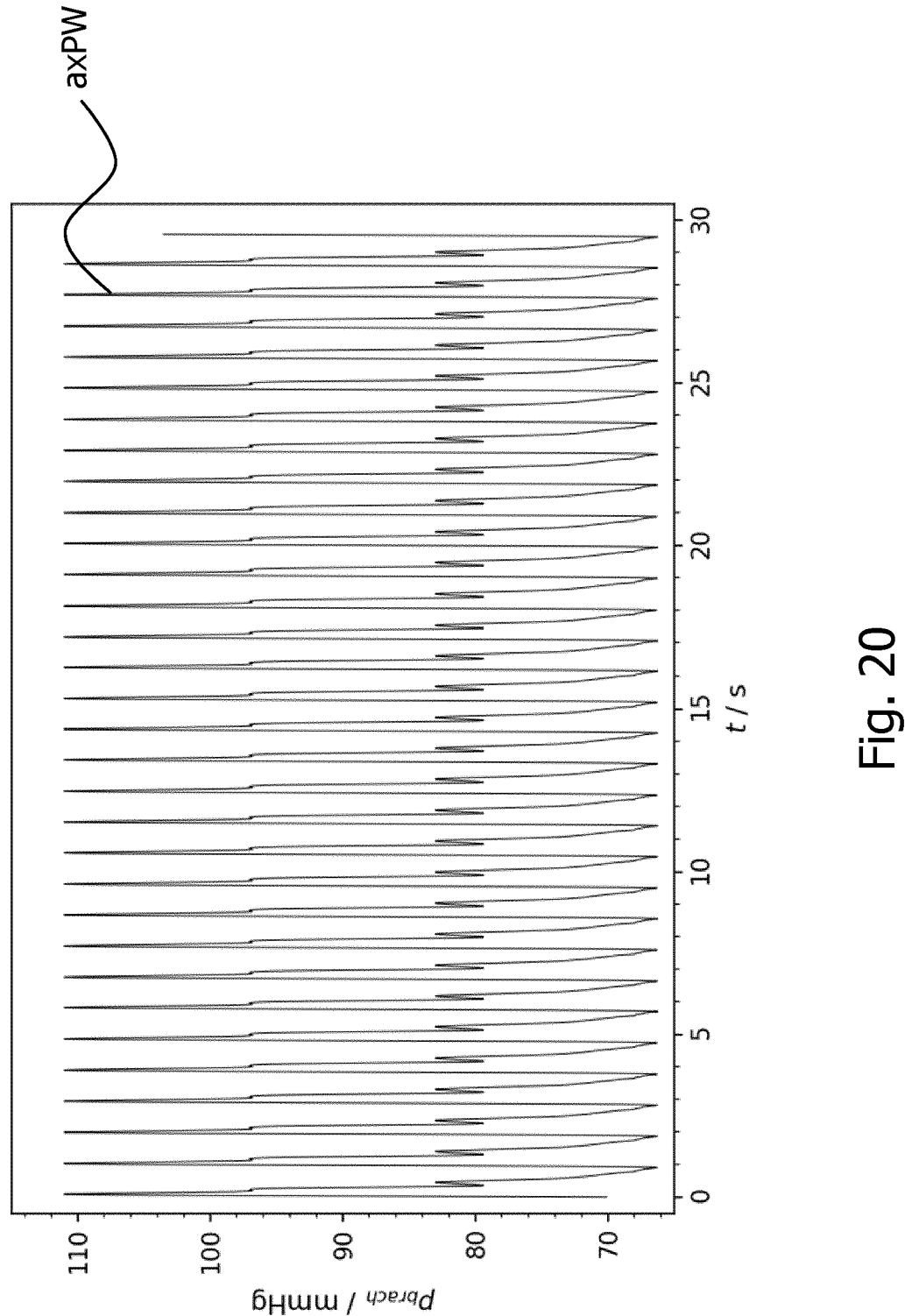
FIG. 20 shows an exemplary PW signal, calculated from the PW signal model by scaling with the blood pressure values $P_{SYS}$ and $P_{DIA}$, as input variable for initialisation.

FIG. 20 shows an example of such an approximated pulse wave signal axPW calculated from the PW signal model by scaling with the blood pressure values $P_{SYS}$ and $P_{DIA}$ as input variable for the initialisation.

Figure 21:
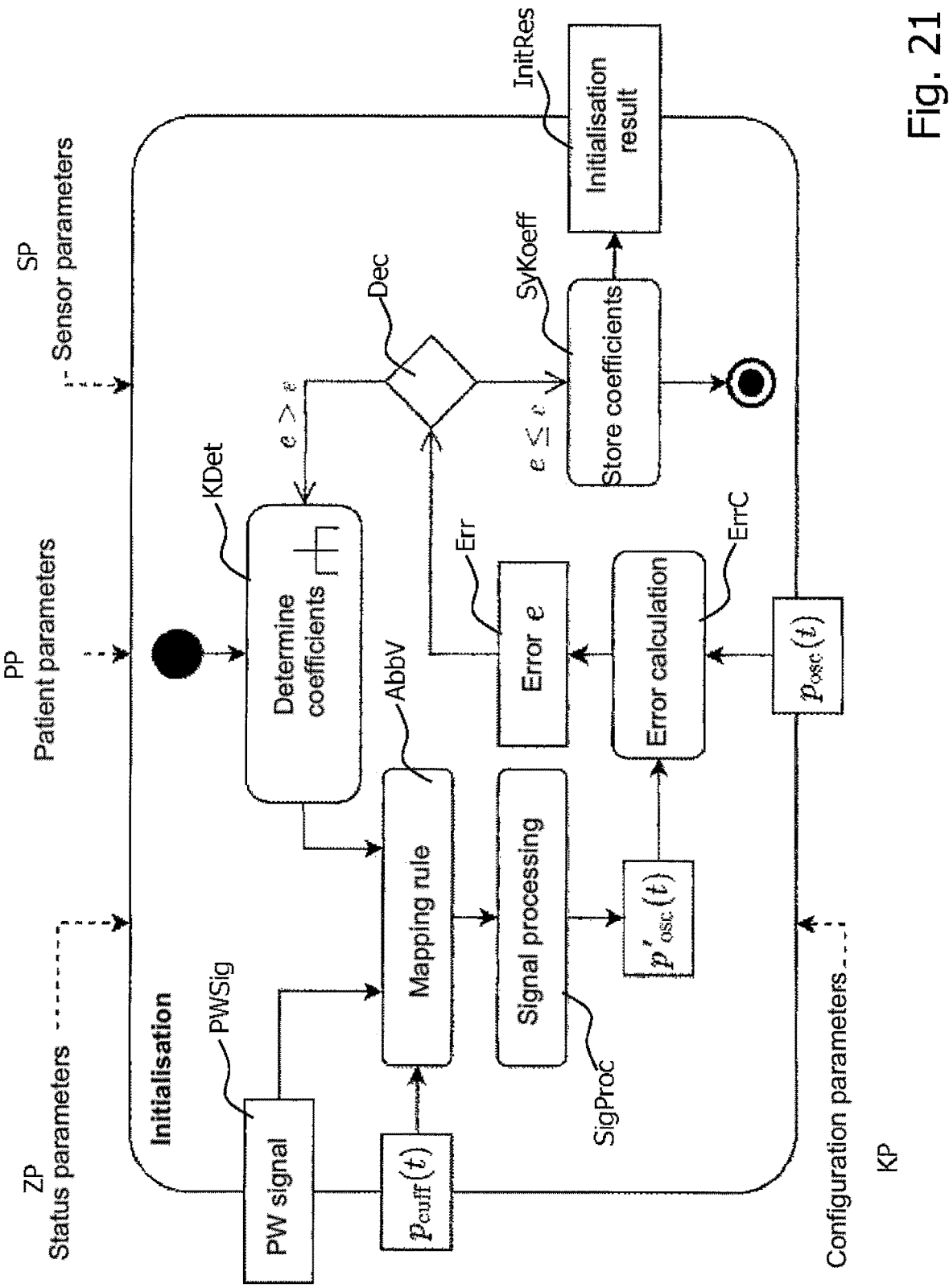
FIG. 21 shows an exemplary sequence of the iterative initialisation for the determination of person-specific coefficients for the mathematical mapping rule modelling the transfer behaviour.

FIG. 21 shows an exemplary sequence of the iterative initialisation I for determining person-specific coefficients for the mathematical mapping rule modelling the transfer behaviour, for example by curve fitting between the calculated ($p'_{osc}$) and the measured ($p_{osc}$) oscillating signal component.

The aim of the initialisation is to determine the coefficient KDet of the person- and sensor-specific transfer function, which describes the transfer behaviour from the peripheral artery (e.g. *A. brachialis*) to the measurement sensor (e.g. pressure sensor in blood pressure cuff), as mentioned beforehand in FIG. 3. The transfer function is described by a mathematical mapping rule, the structure of which can be specified, for example, by a neural network, a filter bank or a differential equation system.

FIG. 21 shows the iterative sequence of the initialisation I for an oscillometric reference measurement, in which the coefficients of the mapping rule are adjusted until the mapping rule transforms the PW signal PWSig, taking into account the cuff pressure $p_{cuff}(t)$, into a calculated response from which an oscillating signal component $p'_{osc}(t)$ can be extracted which has the highest possible agreement with the oscillating signal component $p_{osc}(t)$ extracted from the reference measurement. The iterative process is terminated when the deviation or error e between the calculated and the measured oscillating signal component reaches or falls below a predefined minimum error e.

The initialisation represents an optimisation problem which is to minimise a predefined cost function (deviation between oscillating signal components). This optimisation problem can be solved, for example, with the help of typical global multivariate optimisers.

A model-based approach using a first-order differential equation system to define the structure and behaviour is particularly suitable as a mapping rule.

The process of initialisation I shown here in FIG. 21 is carried out, for example, as follows:

First, a series of status parameters ZP, patient parameters PP of the patient or user, and sensor parameters SP are specified as boundary conditions for the initialisation process. Additional configuration parameters KP concern the manner of initialisation, for example the specification of error bounds, certain iterative approximation methods, and similar parameters.

The pulse wave signal PWSig as well as the applied time-dependent cuff pressure $p_{cuff}(t)$ are transferred with initially given coefficients of the transfer function via a mapping rule AbbV within the scope of a signal processing SigProc into a modelled oscillating signal component $p'_{osc}(t)$.

The modelled oscillating signal component $p'_{osc}(t)$ is compared with the oscillating signal component $p_{osc}(t)$ determined from the reference measurement. This results in an error calculation ErrC and the output Err of an error e.

The error e is subsequently compared in a comparison step Dec with a predefined error bound s. If the error e is greater than the error bound s, the coefficients of the transfer function are re-determined in a new iteration step and a new execution of the coefficient determination KDet.

If the error e is smaller than the error bound s, the now present coefficients of the transfer function are stored in a step SvKoeff and output as initialisation result InitRes.

Figure 22:
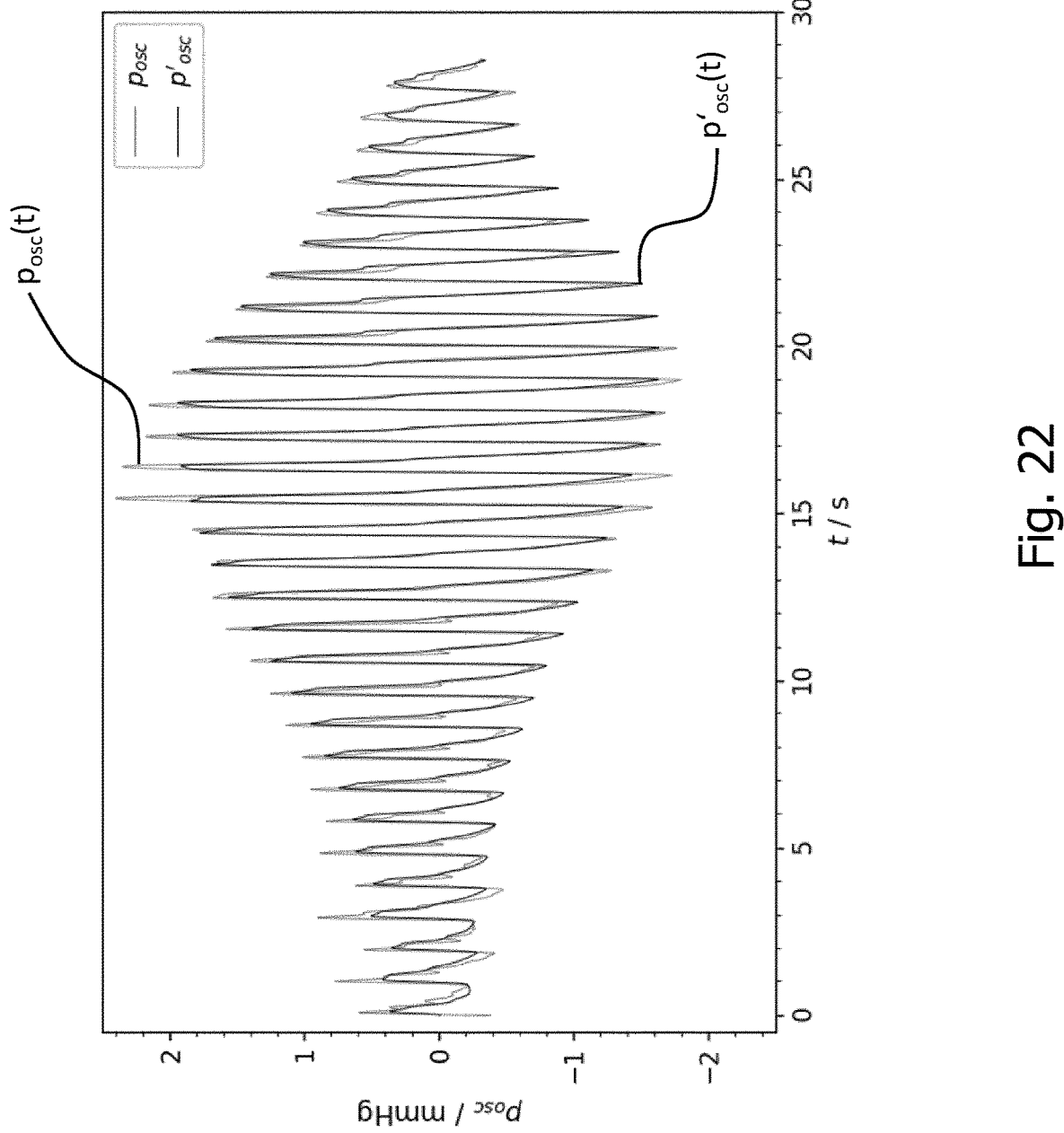
FIG. 22 shows an exemplary result after successful initialisation.

FIG. 22 shows an exemplary result after successful initialisation. The calculated oscillating signal component $p'_{osc}(t)$ and the oscillating signal component $p_{osc}(t)$ extracted from the reference measurement for a complete deflation process of an oscillometric measurement with a blood pressure cuff correspond optimally in their signal curves.

After completion of the initialisation, the coefficients of the transfer function and their statistical uncertainties as well as values/curve parameters for characterising the initialisation process (e.g. value of the cost function, required iterations, etc.) are stored in the initialisation result.

A suitable method for determining the mapping rule between the PW signal and the measurement signal detected by the sensor (consisting of the oscillating and the non-oscillating signal components) is the modelling of the measurement process with the aid of a suitable differential equation system.

For the exemplary embodiment of a cuff-based oscillometric blood pressure measuring apparatus, differential equations for the pressure and volume change in the peripheral artery and for pressure and volume changes in the blood pressure cuff must thus be described mathematically. The establishment of simplified models and associated equation systems to describe the transfer of the arterial volume-pressure signal (i.e. the pulse wave) to the measurement sensor of the blood pressure cuff is known in the literature. The challenge, however, is to adapt the model description and incorporate it into the described method in such a way that an unambiguous relationship is determined between PW features in the arterial pulse wave and the PW features of the pulse-like measured signal at constant, low counter pressure of the low-pressure plateau measurements in the initialisation.

An essential characteristic solution approach is the use of a suitable PW template for the reconstruction of an arterial PW signal model, which reproduces the morphology of the person-specific arterial pulse wave. By using the pulse wave template with the help of the reference blood pressure values available in the initialisation, the problem is simplified to a forward problem in which a response signal is determined from a known source signal. Since source signals (reconstructed arterial PW signal and non-oscillating cuff counter pressure) and response signal are available, the coefficients of the differential equation system modelling the transfer behaviour can be calculated iteratively within the scope of the initialisation. The model parameters are thus determined by solving a multivariate optimisation problem.

Possible coefficients are also called model parameters in the model-based approach and are arranged in a column vector $x=[x_1, x_2, \ldots, x_n]^T$. The model parameters describe both the time-invariant part of the cuff-pressure-dependent transfer function $H_{k,filt}$ and the time-variant part $H_{k,hemo}$, which is dependent on the haemodynamic status of the patient or user.

Figure 23:
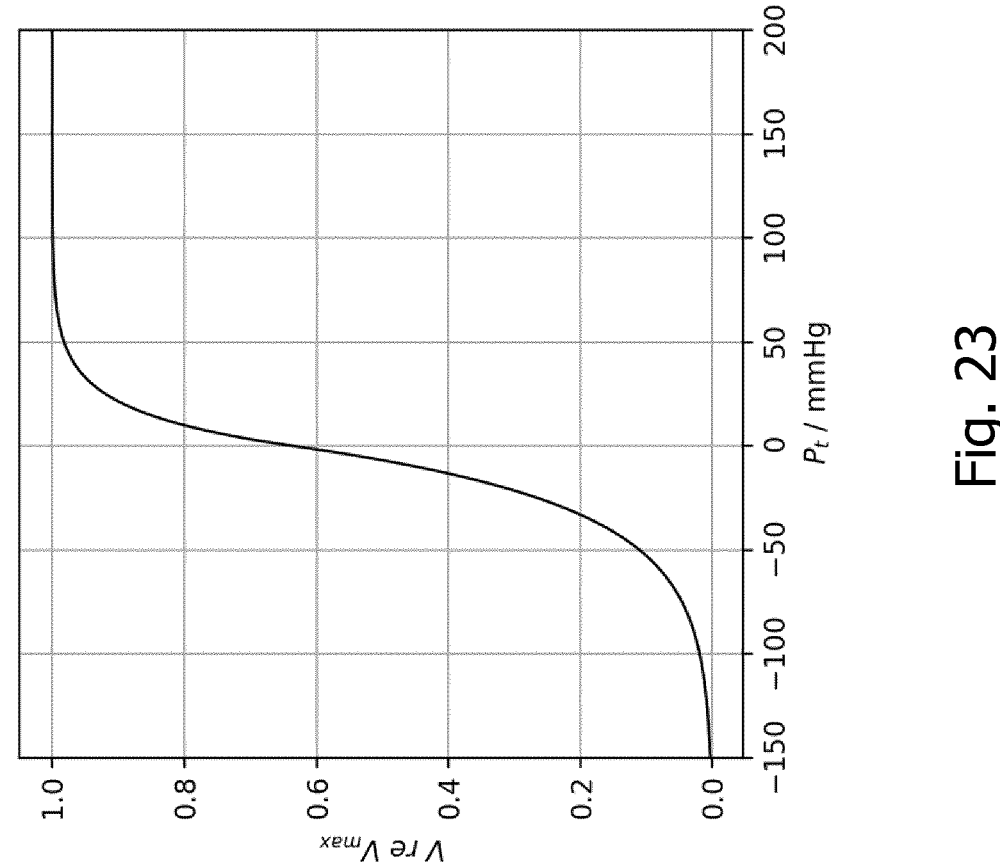
FIG. 23 shows an example of a pressure-volume relationship used in the model-based approach to calculate oscillometric measurement data on the basis of the specified cuff pressure and an arterial PW signal model.

Examples of model parameters of $H_{k,filt}$ are parameters that characterise the dynamic filtering properties of the tissue (and possibly of the sensor) and the general patient-specific transmural pressure-volume relationship of the patient/user. Such a relationship is exemplified in FIG. 23.

Model parameters that characterise the time-variant part $H_{k,hemo}$ are parameters that take into account time-variable effects of the transfer behaviour, e.g. a changed diameter of the peripheral artery due to contraction of the arterial musculature, influences of pharmacological treatment, etc. Changes in the central haemodynamics and effects on the peripheral pulse wave signal are taken into account by transformations of the pulse wave template.

After determining the model parameters, the PW signal reconstructed on the basis of the PW template can be used to calculate the measurement signal detected by the sensor by solving an initial value problem for the given differential equation system. This is shown by way of example in FIG. 24.

Figure 24:
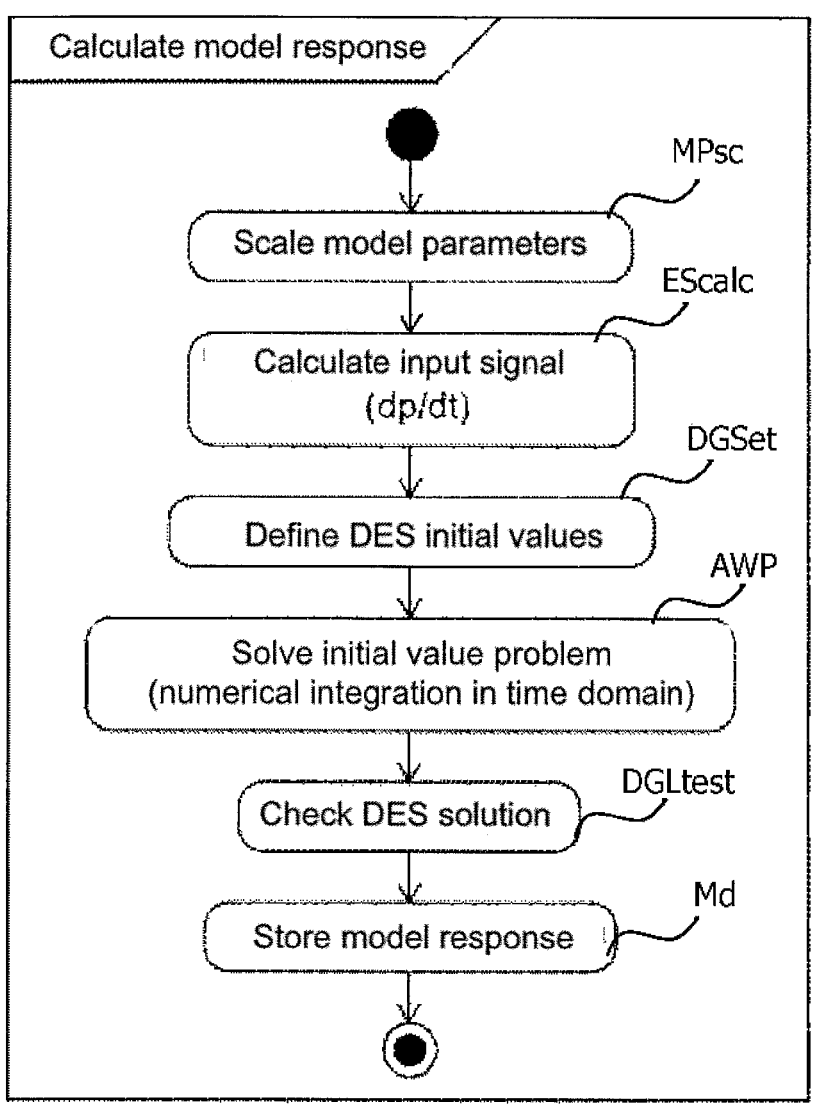
FIG. 24 shows exemplary method steps for calculating the model response as an essential part of initialising and execution of the model-based blood pressure determination.

FIG. 24 shows exemplary method steps for calculating a model response as an essential component of the initialisation on the one hand and thus also of the execution of the model-based blood pressure determination on the other hand.

The measurement process of the blood pressure measurement, for example an oscillometric measurement, is represented by a differential equation system (DES) of $n^{th}$ order. The determination of the model response represents an initial value problem and can be solved by numerical integration of the DES. The model response, which models the measured signal, e.g. the oscillometric measurement signal, is determined by the curve of the arterial pulse wave signal, which is transferred as a derivative to the integrator as an input signal.

If the measurement signal detected with the blood pressure cuff was detected with a change in the non-oscillating cuff pressure, the time-dependent cuff pressure change must be available as an input parameter for the differential equation system. This corresponds to the numerically calculated derivative of the non-oscillating cuff pressure signal $p_{cuff}(t)$. The calculated cuff pressure change can be modified by interpolation, extrapolation and curve fitting. For example, extrapolation can allow a calculation of the model response also in time and pressure domains for which no measurement data are available. The extrapolation can be calculated by different mathematical models.

A possible extension is the determination of a model-based, smoothed cuff pressure change by curve fitting of the cuff pressure change determined from the measurement data using a suitable mathematical model (e.g. linear model, exponential model, polynomial).

The calculation of the model response is thus carried out substantially with the steps of scaling model parameters MPsc, then calculating an input signal EScalc, defining the initial values of the differential equation system DGSet, then solving the initial value problem AWP by a numerical integration in the time domain, checking the determined solution DGLtest and storing the model response Md.

Figure 25:
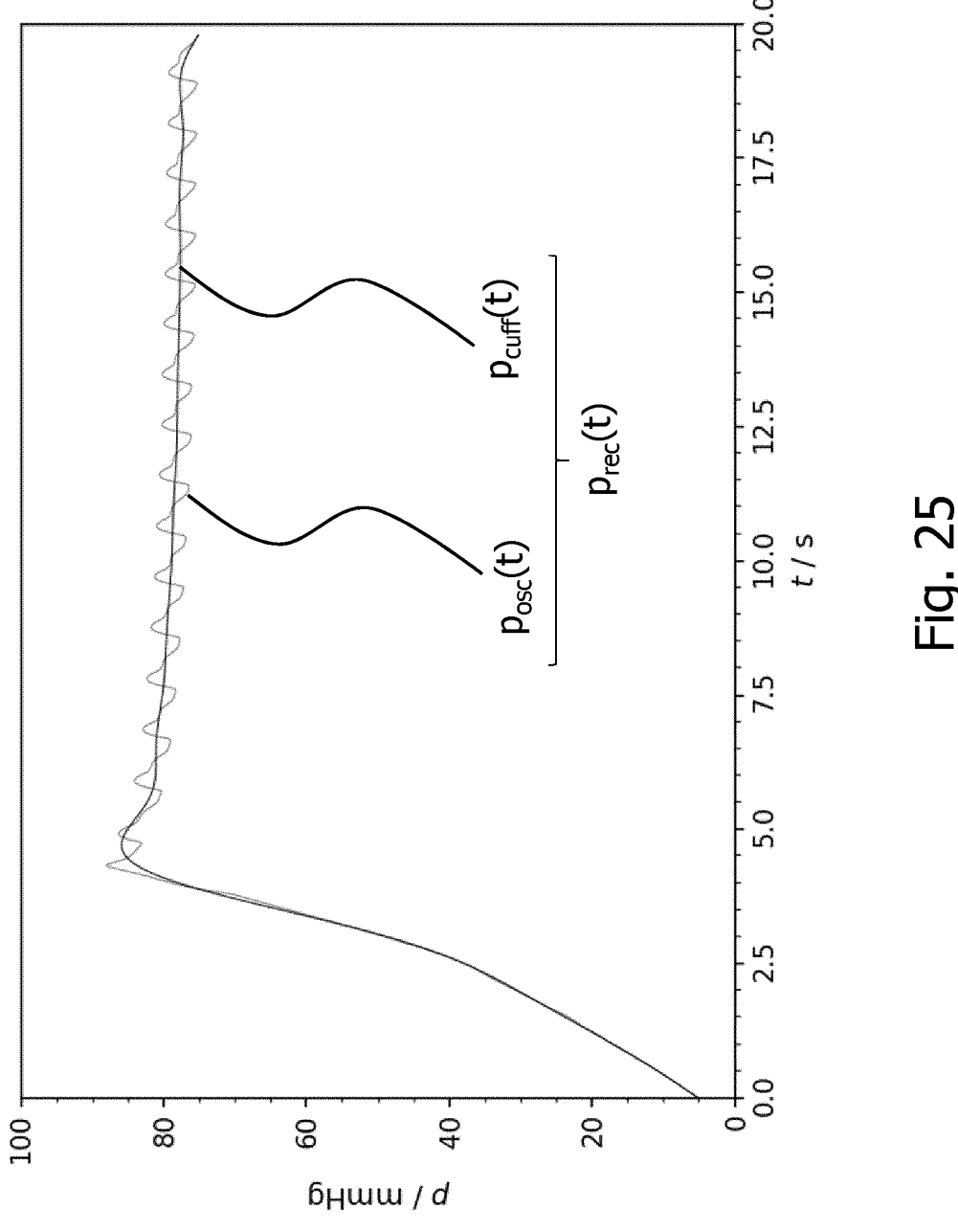
FIG. 25 shows an exemplary oscillometric low-pressure plateau measurement with blood pressure cuff.

After initialisation and determination of the coefficients of the transfer function, the arterial pulse wave can be calculated from the oscillating signal component of the low-pressure plateau measurement using an oscillometric low-pressure plateau measurement as shown in FIG. 25 and the transfer function $H_k(j\omega)$ associated with the constant plateau pressure. FIG. 25 shows an exemplary time curve of a recorded oscillometric low-pressure plateau measurement $p_{rec}(t)$ with blood pressure cuff. This is a superposition of an oscillating signal component $p_{osc}(t)$ and a non-oscillating signal component $P_{cuff}(t)$; $p_{rec}(t)=P_{cuff}(t)+p_{osc}(t)$.

The low-pressure plateau measurement is carried out, for example, in such a way that a pressure is increased to a sub-systolic pressure by means of a cuff and held there constantly at a plateau value for a few seconds. The pressure curve within the time interval of the plateau is evaluated. In order to be able to draw conclusions about the actual pressure conditions in the blood vessel, the transfer function determined during initialisation is inverted and applied to the pressure curves determined during the low-pressure plateau measurement in the sense of solving an inverse problem.

The simple solution of the inverse problem, i.e. the inference to the source signal from an observation according to the equation $$P_{brach}(j\omega) = \frac{P_{osc}(j\omega)}{H_k(j\omega)}$$

is possible for the stationary case if the transfer function and counter pressure are known and constant.

By solving a differential equation system in the time domain, the model-based blood pressure determination also allows the consideration of time-variable counter pressures, i.e. of measurement signals that show no or only weak stationarity.

Figure 26:
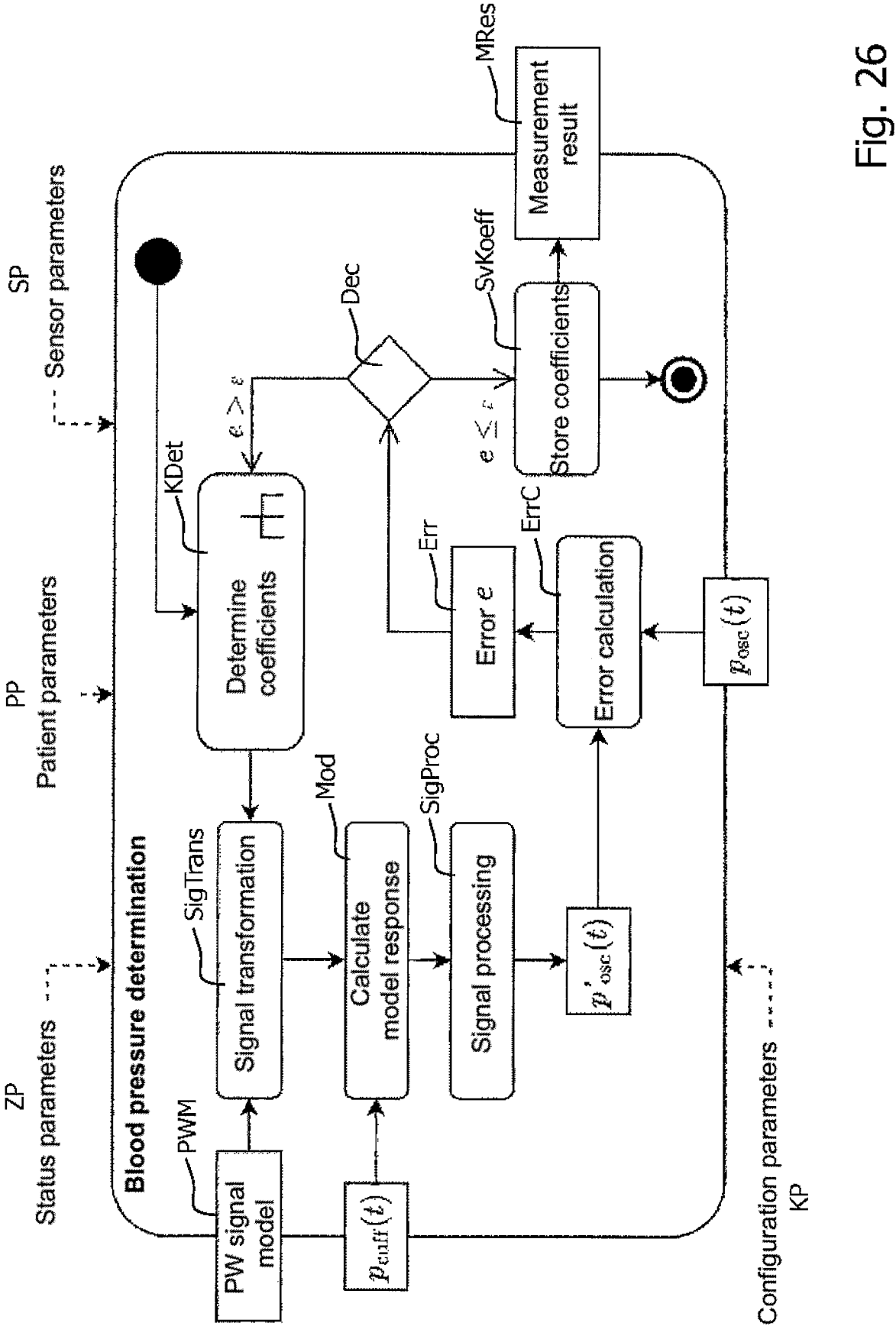
FIG. 26 shows an example of an iterative model-based blood pressure determination.

FIG. 26 shows, analogously to the iterative coefficient determination in the initialisation in FIG. 21, the steps for model-based blood pressure determination, in which the PW signal model is adjusted by a signal transformation (for example by a scaling) until the deviation between the calculated oscillating signal component $p'_{osc}(t)$ and the oscillating signal component $p_{osc}(t)$ determined from the low-pressure plateau measurement becomes minimal. The model response for the predefined PW signal is determined here as shown in FIG. 24. The iterative process can be integrated into a global multivariate optimiser that minimises a cost function. The cost function here represents the deviation between the measured and calculated signal components.

FIG. 26 shows a flow chart of an iterative model-based blood pressure determination in which a PW signal is calculated from the PW signal model PWM using a signal transformation SigTrans. This PW signal, together with the time-variable cuff pressure $p_{cuff}(t)$, forms the input variables for the calculation of the oscillating signal component $p_{osc}(t)$ detected in the low-pressure plateau measurement. The coefficients for the signal transformation of the PW signal model are adjusted by an optimiser until the calculated and measured signal component match or the deviation e reaches or falls below a predefined threshold s. The blood pressures present in the peripheral artery can then be calculated from the coefficients (e.g. offset of the pulse wave, pulse pressure, PW shape distortion factors).

Thus, a pulse wave signal model PWM, the time-variable cuff pressure $p_{cuff}(t)$ and the oscillating signal component $p_{osc}(t)$ are available as input variables for blood pressure determination. In addition, status parameters ZP, patient parameters PP of the patient or user, sensor parameters SP and configuration parameters KP enter the process sequence as boundary conditions.

The data of the PW signal model PWSig are combined with initially present coefficients via a signal transformation SigTrans. The cuff pressure $p_{cuff}(t)$ present during the measurement, together with the data resulting from the signal transformation, is used to determine a model response Mod, which is transformed via a signal processing SigProc into a modelled oscillating component $p'_{osc}(t)$. This can now be compared with the actually measured oscillating component $p_{osc}(t)$. For this purpose, an error calculation ErrC is carried out, which delivers an error e as output Err. This can be compared with a predefined error bound s in a comparison Dec. If the deviation is too large, the coefficients of the PW signal model are reset in a step KDet; if the deviation is within the given tolerance, the coefficients are stored. These then form the measurement result MRes of the blood pressure determination.

In the flow chart according to FIG. 26, a given pulse wave signal model is thus adapted to the measured pulse waves and this adaptation then provides information about the haemodynamic parameters sought.

As shown in the sequence for an exemplary homecare low-pressure blood pressure monitoring in FIG. 5, a validation of the initialisation is performed within the scope of the patient-specific configuration of the blood pressure measuring apparatus.

Figure 27:
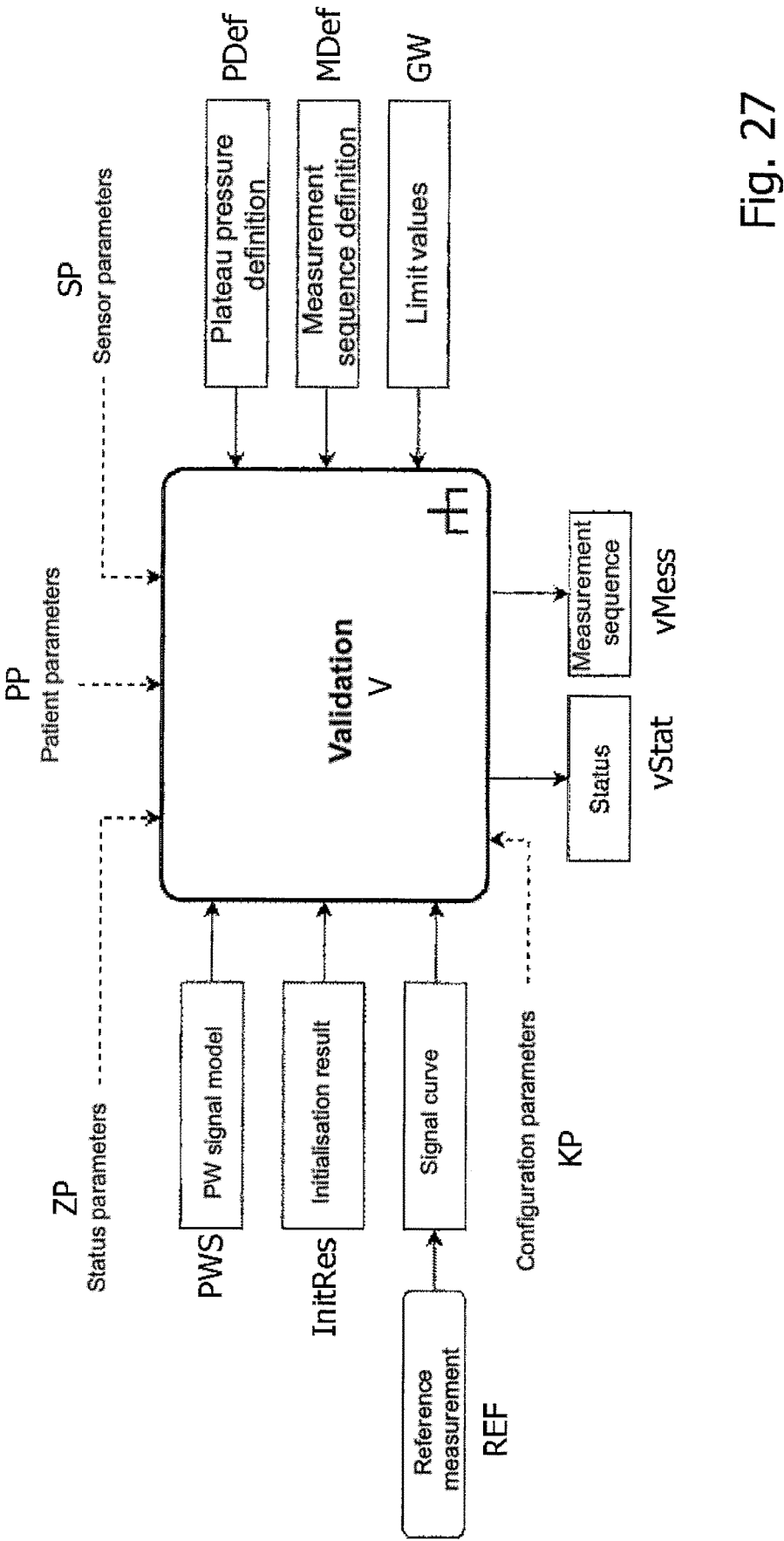
FIG. 27 shows an exemplary input and output parameters for the validation of the initialisation result. Measurement sequence=measurement configuration.

The input and output parameters of the validation are shown schematically in FIG. 27. The aim of the validation is to check the person-specific transfer behaviour determined in the initialisation both for the reference measurement used in the initialisation and for the low-pressure plateau measurements to be used in the measurement period of the low-pressure blood pressure monitoring.

A model-based blood pressure determination is performed according to the previously mentioned exemplary embodiments. The simplest embodiment of the validation is to determine the blood pressure using the reference measurement data and to perform low-pressure plateau measurements for predefined plateau pressure definitions, measurement sequence definitions, e.g. how many plateaus are measured and how often, and limit values. The low-pressure plateau measurement with the highest agreement with the reference values is then selected from the predefined definitions.

The choice of the measurement sequence with the low-pressure plateau measurements to be carried out takes into account the quality and characteristics (if applicable the class) of the pulse waves in the reference signal, the quality of the pulse waves of the associated calculated model response (p'osc) as well as the pulse wave features determined from the PW analysis.

The input parameters of the validation V are first the status parameters ZP, patient parameters PP of the patient or user, sensor parameters PP, and configuration parameters. The metrological input is the pulse wave signal model PWS, the initialisation result InitRes, lastly a reference measurement REF with a corresponding signal curve, a plateau pressure definition PDef, a measurement sequence definition MDef, and limit values GW. The output of the validation is the validated status vStat and the validated measurement sequence vMess.

Figure 28:
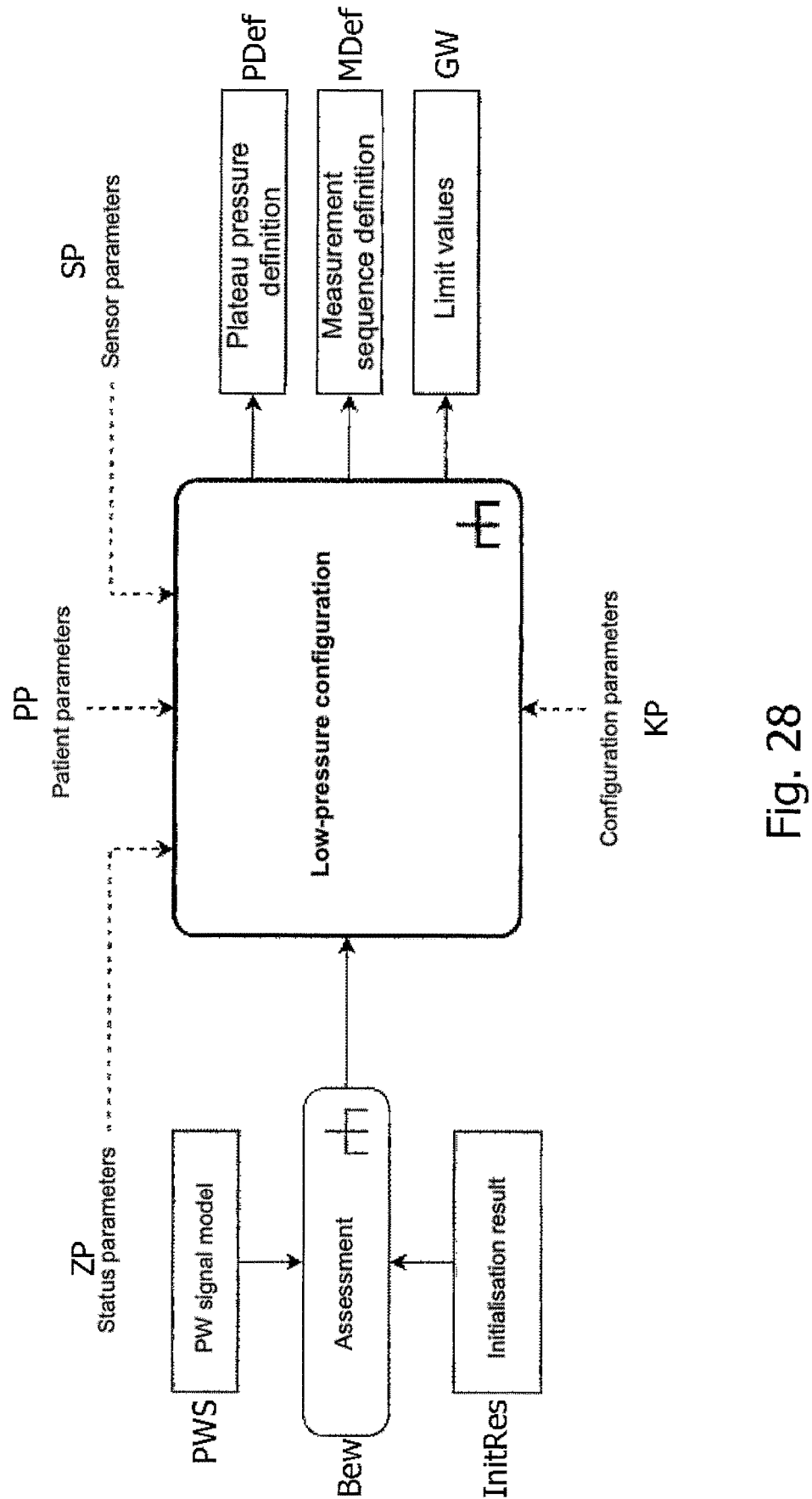
FIG. 28 shows exemplary input and output parameters for the assessment of the initialisation result with individual configuration of any number of low-pressure measurements for blood pressure monitoring.

An extended embodiment of the validation is the derivation of low-pressure plateau measurements directly from the initialisation result InitRes, in which a predefined number of different low-pressure measurements are planned, which are carried out in the validation process and compared against the oscillometric reference measurement as well as with each other. According to FIG. 28, an assessment Bew of the initialisation result is carried out taking into account the person-specific PW signal model PWS, and an individual low-pressure configuration is determined for the patient or user, which contains the plateau pressure definition PDef, measurement sequence definition MDef and limit values GW for the blood pressure determination, which is to be checked in the validation.

In an oscillometric measurement with the determination of the oscillating signal component from a complete deflation process, a plateau reconstruction can be carried out in a further variant by means of a suitable signal transformation. This allows blood pressure determination with a virtual low-pressure plateau measurement, in which the plateau measurement is not physically performed on the patient or user, but is simulated by the control and memory unit of the blood pressure measuring apparatus. This allows the optimal low-pressure configuration to be found for the patient or user without the need for a large number of additional measurements. The optimal low-pressure configuration includes the measurement parameters (e.g. constant counter pressure) and the number of low-pressure plateau measurements to be performed and is stored in the measurement sequence. The search for the optimal low-pressure configuration performed by the blood pressure measuring apparatus is also referred to as dynamic [individual]configuration and defines the measurement sequence for blood pressure monitoring.

The method for operating a blood pressure measuring apparatus is thus carried out, in summary, in particular with the following method steps:

Applying a measuring apparatus with a pressure measuring unit and possibly a pressure unit to a measurement point on the body.

Initialising the measuring apparatus by carrying out a reference measurement and/or by carrying out defined position changes of the measurement point and determining person- and sensor-specific parameters characterising the pulse wave transfer of the peripheral artery to the measurement sensor, wherein the following steps are carried out:

a) Increasing the sampling rate by interpolation of the temporal signal curve detected by the sensor.

b) Separating the interpolated signal curve into a non-oscillating and an oscillating (pulse-like) signal component.

c) Performing an individual artefact detection for the extracted signal components.

d) Reducing and/or excluding the detected artefacts in the extracted signal components.

e) Performing a signal analysis of the pulse-like signal component to characterise the signal dynamics and extract various signal features, in particular the foot points of the pulse waves occurring in the pulse-like signal component.

f) Aligning the pulse-like signal component with detected signal features by interpolation of the signal curve.

g) Decomposing an aligned, pulse-like signal component into data over individual periods to identify individual pulse waves.

h) Classifying and performing a quality assessment of the individual pulse waves on the basis of pulse wave morphology and the individual pulse wave features.

i) Forming a pulse wave template from a suitable sub-set of the classified pulse waves and pulse wave features by a signal transformation (mathematical mapping rule) to describe the characteristics of the arterial pulse wave form.

j) Reconstructing a pulse wave signal model time-synchronous to the detected reference signal, taking into account the time-variant periodicity of the pulse-like signal component of the reference signal.

k) Reconstructing an arterial pulse wave signal by scaling the signal model with the blood pressure parameters known from the reference measurements.

l) Determining the individual transfer characteristic by iterative adjustment of person-specific parameters that maps the reconstructed, scaled signal model as accurately as possible to the detected reference signal.

Storing the person-specific initialisation parameters in a memory and control unit.

Performing at least one blood pressure measurement in the presence of a counter pressure through the pressure unit in a sub-systolic low-pressure range.

Maintaining the counter pressure present within a plateau phase having a predetermined duration and registering temporal blood pressure curve data during the predetermined duration.

Converting the registered temporal blood pressure curve data into temporal arterial blood pressure data via the initialisation parameters, wherein the following steps are carried out:

a) Processing steps of the signal analysis a) to f) of the initialisation, but for the blood pressure curve data of the plateau phase detected in the sub-systolic low-pressure range.

b) Reconstructing a pulse wave signal model time-synchronous to the detected blood pressure curve data from the pulse wave template generated in the initialisation.

c) Reconstructing an arterial pulse wave signal in the control and memory unit with the aid of the individual transfer parameters by means of an iterated model-based blood pressure determination, wherein a deviation-minimising adaptation of parameters of a pulse wave signal model to the oscillating signal component of the measured blood pressure curve data is performed via a signal transformation.

d) Extracting features from the calculated, peripheral arterial pulse wave signal.

e) Evaluating the extracted features to determine the peripheral blood pressure and other haemodynamic parameters such as pulse wave velocity, arterial age, cardiac output, etc.

Reinitialising the method if the arterial pulse wave determined during the measurement period or the associated blood pressure values or haemodynamic parameters exceed or fall below the limit values defined in the initialisation.

The described method is used to determine and analyse pulse waves, and to determine blood pressure and other haemodynamic parameters. After initialisation, the blood pressure curve data necessary for this purpose are implemented in the sub-systolic low-pressure range, which is load-free for the patient or user.

The subject of the invention has been explained on the basis of exemplary embodiments. Further embodiments can also be found in the dependent claims. Further embodiments are possible within the capabilities of a person skilled in the art.

LIST OF REFERENCE SIGNS

1 external evaluation unit
10 display
11 configuration program
12 evaluation program
13 user interface
14 device interface
2 control and memory unit
20 display
21 initialisation program
22 control program
23 memory
24 processor with bus
25 digital signal-processing processor
27 interface
29 interface to external evaluation unit
3 measuring unit, initialisation unit and measuring unit
30 fastening apparatus
31 sensor
32 actuator
33 buffer
34 interface
4 interface connection
5 interface connection
6 test subject
A display of the measurement values
AbbV mapping rule
Au inflation process
AufInt inflation interval
AbInt deflation interval
Ab deflation process
Dec comparison step
DGLtest checking of the determined solution
DGSet setting of differential equation system initial values
e error
EpM single-spot low-pressure plateau measurement
Err output error
ErrC error calculation
EScalc input signal calculation
FP foot point
FPAdj foot point alignment
GW limit value
I initialisation
InitRes initialisation result KDet coefficient determination
KP configuration parameters
M oscillometric measurement
Max maximum
Min minimum
Md storing of model response
MDef measurement sequence definition
MEx feature extraction
MP medical staff
MZu feature assignment
pM plateau measurement
aG active counter pressure control
aS active measurement sensor
pS passive measurement sensor
PDef plateau pressure definition
PP patient parameters
PW pulse waves, extracted
axPW approximated pulse wave signal
PWA pulse wave analysis
PWClas pulse wave classification
PWEx pulse wave extraction
PWM pulse wave features
PWMod pulse wave signal model
PWScal pulse wave scaling
PWSig pulse wave signal
PWSlc pulse wave selection
PWVo pulse wave template
QB quality assessment
REF reference measurement
ROI regions of interest
S sensor check
SigComp signal components
SigProc signal processing
SigTrans signal transformation
SP sensor parameters
St auscultation
SvKoeff storing of coefficients
T tangent curve
V validation
vMess validated measurement sequence
vStat validated status
W inflection points
ZP status parameters

The invention claimed is:

1. A method for operating a blood pressure measuring apparatus comprising the following method steps:
    applying the blood pressure measuring apparatus to a measuring point on the body, wherein the blood pressure measuring apparatus contains a pressure measuring unit and a pressure unit;
    initialising the blood pressure measuring apparatus by carrying out a reference measurement and determining person-specific initialisation parameters;
    storing the person-specific initialisation parameters in a memory and control unit;
    performing at least one blood pressure measurement in the presence of a counter pressure through the pressure unit in a sub-systolic range;
    maintaining the counter pressure within a sub-systolic plateau phase for a predetermined duration and registering first temporal blood pressure curve data during the predetermined duration;
    converting the registered first temporal blood pressure curve data into temporal arterial blood pressure data via the initialisation parameters,
wherein the initialisation is carried out by performing the reference measurement with the following steps:
    applying a measurement pressure to the blood pressure measuring apparatus in a defined pressure range;
    changing in a defined way the measurement pressure from the blood pressure measuring apparatus and registering second temporal pressure curve data in the control and memory unit;
    extracting an oscillating pulse component from the second temporal pressure curve in conjunction with a storing of a series of data regarding individual pulse waves in the control and memory unit;
    performing a signal analysis of the individual pulse waves and a data comparison with a pulse wave signal model by the control and memory unit;
    determining a first person-specific transfer function and coefficients thereof from the data comparison and storing the determined transfer function as one of the person-specific initialisation parameters in the control and memory unit,
wherein
after the initialisation and the determination of the coefficients of the first transfer function,
a second transfer function Hk(jω) is determined for a constant cuff pressure using the coefficients known from the initialization; and
an arterial pulse wave is calculated from an oscillating signal component of a sub-systolic plateau measurement using an oscillometric sub-systolic plateau measurement and the second transfer function Hk(jω) for constant cuff pressure associated with constant plateau pressure; and
wherein
the signal analysis of the individual pulse waves is performed with the following steps:
    evaluating a form of each of the individual pulse waves and classifying each of the individual pulse waves in question in an evaluation unit and storing each of the individual pulse waves in an internal memory;
    assembling and transforming pulse waves from at least one classification into the pulse wave signal model reproducing features of the arterial pulse wave; and
    adapting measured pulse wave curves to the at least one pulse wave signal model and determining at least one specific transfer function for the particular pulse wave signal model.

2. The method according to claim 1,
wherein
a validation of the person-specific transfer function is carried out, wherein second blood pressure curve data determined and stored during a validation blood pressure measurement at a given counter pressure are compared with given reference parameters.

3. The method according to claim 1,
wherein
the at least one blood pressure measurement in the sub-systolic range includes conversion of measured temporal blood pressure values into arterial blood pressure values in the control and memory unit based on an inversion of the person-specific transfer function determined from the initialisation step.

4. The method according to claim 1,
wherein
the at least one blood pressure measurement in the sub-systolic range includes carrying out an iterated model-based blood pressure determination in the control and memory unit, wherein a deviation-minimising adaptation of parameters of the pulse wave signal model to the oscillating signal component of the measured blood pressure is performed via a signal transformation.

5. The method according to claim 1,
wherein
in a validation of the initialisation parameters, a model-based blood pressure determination is carried out in the sub-systolic range and is compared with the pulse wave signal model and a signal curve from the reference measurement, wherein an initialisation result is compared with the provided initialisation parameters.

6. The method according to claim 1,
wherein
the reference measurement is carried out by an invasive blood pressure measuring catheter, located in a blood vessel, wherein a time curve of blood pressure is determined and is compared with a temporal pressure curve determined in parallel at the blood pressure measuring apparatus in order to determine the at least one specific transfer function for the pulse wave signal model, wherein the pulse wave signal model is scaled so that a resulting calculated pulse wave signal approximates the arterial pulse wave as accurately as possible.

7. The method according to claim 1,
wherein
for the initialisation and/or the at least one blood pressure measurement, an inflatable pressure cuff or a combination of a pressure cuff and a garment exerting a constant sub-systolic pressure is used as the pressure unit of the blood pressure measuring apparatus.

8. The method according to claim 1,
wherein
an inflatable pressure cuff in combination with an optical or electromagnetic sensor is used as the pressure unit of the blood pressure measuring apparatus, wherein the inflatable pressure cuff is used for carrying out the reference measurement and the sensor is used for the at least one blood pressure measurement in the sub-systolic range.

* * * * *